US010016364B2

(12) United States Patent
Nicolosi et al.

(10) Patent No.: US 10,016,364 B2
(45) Date of Patent: Jul. 10, 2018

(54) COMPOSITIONS AND METHODS FOR MAKING AND USING NANOEMULSIONS

(71) Applicant: University of Massachusetts Lowell, Lowell, MA (US)

(72) Inventors: Robert James Nicolosi, Nashua, NH (US); Thomas Wilson, Bradford, MA (US)

(73) Assignee: University of Massachusetts Lowell, Boston, MA (US)

(*) Notice: Subject to any disclaimer, the term of this patent is extended or adjusted under 35 U.S.C. 154(b) by 0 days.

(21) Appl. No.: 14/594,417

(22) Filed: Jan. 12, 2015

(65) Prior Publication Data

US 2015/0335574 A1 Nov. 26, 2015

Related U.S. Application Data

(63) Continuation of application No. 11/996,016, filed as application No. PCT/US2006/026918 on Jul. 11, 2006.

(60) Provisional application No. 60/700,224, filed on Jul. 18, 2005.

(51) Int. Cl.
*A61K 9/107* (2006.01)
*B01F 3/08* (2006.01)

(52) U.S. Cl.
CPC .... *A61K 9/1075* (2013.01); *B01F 2003/0849* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 4,075,196 A * | 2/1978 | Badertscher | A23J 1/202 530/360 |
| 4,533,254 A | 8/1985 | Cook et al. | |
| 4,908,154 A | 3/1990 | Cook et al. | |
| 5,152,923 A | 10/1992 | Weder et al. | |
| 5,302,401 A * | 4/1994 | Liversidge | A61K 9/146 424/489 |
| 5,374,614 A | 12/1994 | Behan et al. | |
| 5,401,243 A | 3/1995 | Borodic | |
| 5,502,045 A | 3/1996 | Miettinen et al. | |
| 5,510,118 A * | 4/1996 | Bosch | A61K 9/146 424/488 |
| 5,554,372 A * | 9/1996 | Hunter | A61K 39/385 424/278.1 |
| 5,576,016 A | 11/1996 | Amselem et al. | |
| 5,629,021 A | 5/1997 | Wright | |
| 5,651,991 A | 7/1997 | Sugiyama et al. | |
| 5,652,274 A | 7/1997 | Martin | |
| 5,670,484 A | 9/1997 | Binder | |
| 5,672,358 A | 9/1997 | Tabibi et al. | |
| 5,753,241 A | 5/1998 | Ribier et al. | |
| 5,766,605 A | 6/1998 | Sanders et al. | |
| 5,851,452 A | 12/1998 | Vallet Mas et al. | |
| 5,858,410 A | 1/1999 | Muller et al. | |
| 5,925,341 A | 7/1999 | Cervantes et al. | |
| 5,932,562 A | 8/1999 | Ostlund, Jr. | |
| 5,993,852 A * | 11/1999 | Foldvari | A61K 9/127 264/41 |
| 5,994,414 A | 11/1999 | Franco et al. | |
| 6,007,856 A | 12/1999 | Cox et al. | |
| 6,039,936 A | 3/2000 | Restle et al. | |

(Continued)

FOREIGN PATENT DOCUMENTS

| | | |
|---|---|---|
| CA | 2494473 A1 | 4/2005 |
| CA | 2543722 A1 | 5/2005 |

(Continued)

OTHER PUBLICATIONS

S Pinnamaneni, NG Das, SK Das. "Comparison of oil-in-water emulsions manufactured by microfluidization and homogenization." Pharmazie, vol. 58(8), 2003, pp. 554-558.*

(Continued)

*Primary Examiner* — Isaac Shomer
(74) *Attorney, Agent, or Firm* — McCarter & English, LLP; Marcie B. Clarke; Joshua J. Galgano

(57) ABSTRACT

The present invention discloses an improved nanoemulsion comprising a uniform and discrete range of very small particle nano-sized diameters. This uniformity results in improved bioavailability of incorporated compounds (i.e., pharmaceuticals or nutraceuticals) as reflected in various pharmacokinetic parameters including, but not limited to, decreased Tmax, increased CmaX3 and increased AUC. The improved method of making these uniform nanoemulsions utilizes microfluidization which differs in both process and mechanics when compared to conventional milling and grinding techniques used to generate nanoparticulate compositions. Further, the improvement results, in part, from a novel step of mixing a substantially soluble compound into a heated dispersion medium. This is unlike current nanoparticulate composition methods that mix an insoluble compound with an unheated dispersion medium. Further, these nanoemulsions are observed to be bacterial-resistant and stable to extremes in both temperature and pH changes. Consequently, these nanoemulsions are expected to have a significantly prolonged shelf-life than currently available nanoemulsions.

15 Claims, 13 Drawing Sheets

(56) References Cited

U.S. PATENT DOCUMENTS

| | | |
|---|---|---|
| 6,165,500 A | 12/2000 | Cevc |
| 6,224,853 B1 | 5/2001 | Steel et al. |
| 6,265,180 B1 | 7/2001 | Zuelli et al. |
| 6,274,150 B1 | 8/2001 | Simonnet et al. |
| 6,312,708 B1 | 11/2001 | Donovan |
| 6,358,917 B1 | 3/2002 | Carruthers et al. |
| 6,387,411 B2 | 5/2002 | Bruce et al. |
| 6,429,189 B1 | 8/2002 | Borodic |
| 6,558,941 B2 | 5/2003 | Zuelli et al. |
| 6,573,241 B1 | 6/2003 | Bigalke et al. |
| 6,589,588 B1 | 7/2003 | Wester et al. |
| 6,623,780 B1 | 9/2003 | Stevens et al. |
| 6,632,440 B1 | 10/2003 | Quinn et al. |
| 6,670,322 B2 | 12/2003 | Goodnough et al. |
| 6,688,311 B2 | 2/2004 | Hanin |
| 6,720,001 B2 | 4/2004 | Chen et al. |
| 6,835,395 B1 | 12/2004 | Semple et al. |
| 6,861,066 B2 | 3/2005 | Van de Casteele |
| 6,869,610 B2 | 3/2005 | Aoki et al. |
| 6,902,737 B2 | 6/2005 | Quemin |
| 6,939,852 B2 | 9/2005 | Graham |
| 6,974,578 B1 | 12/2005 | Aoki et al. |
| 6,974,579 B2 | 12/2005 | Brin et al. |
| 7,001,602 B2 | 2/2006 | Schmidt |
| RE39,086 E | 5/2006 | Carruthers et al. |
| 7,226,605 B2 | 6/2007 | Suskind et al. |
| 7,228,259 B2 | 6/2007 | Freund |
| 7,255,865 B2 | 8/2007 | Walker |
| 7,384,918 B2 | 6/2008 | Graham |
| 7,507,419 B2 | 3/2009 | Coleman, III |
| 7,763,663 B2 | 7/2010 | McCarthy et al. |
| 8,318,181 B2 | 11/2012 | Edelson et al. |
| 2002/0015721 A1 | 2/2002 | Simonnet et al. |
| 2002/0048596 A1 | 4/2002 | Cevc |
| 2002/0098215 A1 | 7/2002 | Douin et al. |
| 2002/0107199 A1 | 8/2002 | Walker |
| 2002/0155084 A1 | 10/2002 | Roessler et al. |
| 2002/0165179 A1 | 11/2002 | Baker |
| 2003/0072801 A1 | 4/2003 | Curatolo et al. |
| 2003/0108597 A1 | 6/2003 | Chancellor et al. |
| 2003/0113349 A1 | 6/2003 | Coleman |
| 2003/0138465 A9 | 7/2003 | Douin et al. |
| 2003/0194412 A1 | 10/2003 | Baker et al. |
| 2003/0206955 A1 | 11/2003 | Sonneville-Aubrun et al. |
| 2003/0224020 A1 | 12/2003 | Zabudkin et al. |
| 2004/0003324 A1 | 1/2004 | Uhlig |
| 2004/0005370 A1 | 1/2004 | Breton |
| 2004/0009180 A1 | 1/2004 | Donovan |
| 2004/0009936 A1 | 1/2004 | Tang |
| 2004/0033202 A1 | 2/2004 | Cooper et al. |
| 2004/0033241 A1 | 2/2004 | Donovan |
| 2004/0037853 A1 | 2/2004 | Borodic |
| 2004/0048836 A1 | 3/2004 | Wilmott |
| 2004/0081688 A1 | 4/2004 | Del Curto et al. |
| 2004/0115159 A1 | 6/2004 | Tadlock et al. |
| 2004/0115727 A1 | 6/2004 | Steward et al. |
| 2004/0116512 A1* | 6/2004 | Naguib ............... A61K 31/355 514/458 |
| 2004/0126397 A1 | 7/2004 | Aoki et al. |
| 2004/0127661 A1 | 7/2004 | Kaspar et al. |
| 2004/0151741 A1 | 8/2004 | Borodic |
| 2004/0229038 A1 | 11/2004 | Cooper et al. |
| 2004/0258701 A1* | 12/2004 | Dominowski ....... A61K 9/1075 424/184.1 |
| 2004/0258758 A1 | 12/2004 | Gustow et al. |
| 2005/0048088 A1 | 3/2005 | Zulli et al. |
| 2005/0074461 A1 | 4/2005 | Donovan |
| 2005/0074466 A1 | 4/2005 | Suskind et al. |
| 2005/0079131 A1 | 4/2005 | Lanza et al. |
| 2005/0096340 A1 | 5/2005 | Zhang et al. |
| 2005/0123897 A1 | 6/2005 | Cevc et al. |
| 2005/0142150 A1 | 6/2005 | Graham |
| 2005/0147688 A1 | 7/2005 | Russell |
| 2005/0175636 A1 | 8/2005 | Donovan |
| 2005/0184275 A1 | 8/2005 | Mora-Gutierrez et al. |
| 2005/0196414 A1 | 9/2005 | Dake et al. |
| 2005/0208083 A1 | 9/2005 | Annis |
| 2005/0214325 A1 | 9/2005 | David |
| 2005/0226842 A1 | 10/2005 | Douin et al. |
| 2005/0249686 A1 | 11/2005 | Pataut et al. |
| 2005/0261632 A1 | 11/2005 | Xu |
| 2006/0018931 A1 | 1/2006 | Taylor |
| 2006/0057165 A1 | 3/2006 | Dimitrakoudis et al. |
| 2006/0073208 A1 | 4/2006 | First |
| 2006/0093624 A1 | 5/2006 | Graham |
| 2006/0153876 A1 | 7/2006 | Sanders |
| 2006/0153877 A1 | 7/2006 | Kozaki et al. |
| 2006/0165657 A1 | 7/2006 | Bernasconi et al. |
| 2006/0182767 A1 | 8/2006 | Borodic |
| 2006/0188525 A1 | 8/2006 | Donovan |
| 2007/0036831 A1 | 2/2007 | Baker |
| 2007/0116723 A1 | 5/2007 | Coleman |
| 2007/0148194 A1 | 6/2007 | Amiji et al. |
| 2007/0178121 A1 | 8/2007 | First et al. |
| 2008/0274195 A1 | 11/2008 | Nicolosi et al. |
| 2009/0306198 A1 | 12/2009 | Nicolosi et al. |
| 2010/0040883 A1 | 2/2010 | McCarthy et al. |
| 2010/0183726 A1 | 7/2010 | Nicolosi et al. |
| 2011/0020227 A1 | 1/2011 | McCarthy et al. |
| 2011/0206736 A1 | 8/2011 | Waldman et al. |
| 2011/0206739 A1 | 8/2011 | Nicolosi et al. |
| 2012/0164182 A1 | 6/2012 | Edelson et al. |
| 2014/0099342 A1 | 4/2014 | Edelson et al. |

FOREIGN PATENT DOCUMENTS

| | | |
|---|---|---|
| CA | 2554052 A1 | 8/2005 |
| CN | 1130868 A | 9/1996 |
| EP | 0315079 A1 | 5/1989 |
| EP | 0572080 A1 | 12/1993 |
| EP | 0770422 A1 | 5/1997 |
| EP | 1080720 A1 | 3/2001 |
| EP | 1249232 A1 | 10/2002 |
| EP | 1652515 A1 | 5/2006 |
| JP | H02203 A | 1/1990 |
| JP | 2001513331 A | 9/2001 |
| JP | 2003527411 A | 9/2003 |
| JP | 2004532214 A | 10/2004 |
| KR | 20020079150 A | 10/2002 |
| WO | 94/20072 A1 | 9/1994 |
| WO | 95/22973 A1 | 8/1995 |
| WO | 98/51278 A2 | 11/1998 |
| WO | 99/07238 A2 | 2/1999 |
| WO | 00/38653 A1 | 7/2000 |
| WO | 01/10413 A2 | 2/2001 |
| WO | 01/70197 A2 | 9/2001 |
| WO | 02/056866 | 7/2002 |
| WO | 2002/080864 A1 | 10/2002 |
| WO | 2003/101483 A1 | 12/2003 |
| WO | 2004/006954 A2 | 1/2004 |
| WO | 2004/076634 A2 | 9/2004 |
| WO | 2004/084839 A2 | 10/2004 |
| WO | 2005/013938 A1 | 2/2005 |
| WO | 2005/020962 A1 | 3/2005 |
| WO | 2005/027872 A2 | 3/2005 |
| WO | 2005/042539 A1 | 5/2005 |
| WO | 2005/063377 A1 | 7/2005 |
| WO | 2005/070394 A2 | 8/2005 |
| WO | 2005/084361 A2 | 9/2005 |
| WO | 2005/102285 A1 | 11/2005 |
| WO | 2006/005910 A2 | 1/2006 |
| WO | 2006/050926 A2 | 5/2006 |
| WO | 2006/084353 A1 | 8/2006 |
| WO | 2006/094263 A2 | 9/2006 |
| WO | 2006/138127 A2 | 12/2006 |
| WO | 2007/041664 A1 | 4/2007 |

(56) References Cited

FOREIGN PATENT DOCUMENTS

| WO | 2007/089454 A2 | 8/2007 |
|---|---|---|
| WO | 2007/103555 A2 | 9/2007 |
| WO | 2008/010788 A2 | 1/2008 |

OTHER PUBLICATIONS

I Gunniss. "Microfluidics Webinar Series." "Principles of Particle Size Reduction and Characterization." http://www.horiba.com/fileadmin/uploads/Scientific/Documents/PSA/Webinar_Slides/TE007.pdf, accessed by examiner on Mar. 24, 2017, 42 printed pages.*
CAS Registry Record for Zeaxanthin (CAS # 144-68-3). Entered STN Nov. 16, 1984, 5 printed pages.*
Badea et al., In vivo cutaneous interferon-gamma gene delivery using novel dicationic (Gemini) surfactant-plasmid complexes, J. Gene Med., 7:1200-1214 (2005).
Bos and Meinardi, "The 500 Dalton rule for the skin penetration of chemical compounds and druqs," Exp. Dermatol., 9:165-169 (2000).
Chen et al., "Transdermal protein delivery by a coadministered peptide identified via phage array," Nature Biotechnoloqy, 24(4):455-459 (2006).
Choi et al., Percutaneous Absorption, Fourth Edition, Vo. 155, Bronaugh and Maibach ed., Taylor and Francis, Boca Ratonm Florida, 2005, Index and Table of contents only, 33 pages.
Dalgleish et al., "The characterization of small emulsion droplets made from milk proteins and triglyceride oil," Colloids and Surfaces, Physiachemical and Engineering Aspects, Elsevier, 123-124:145-153, 1997.
De Campo, et al., "Five-component food-grade microemulsions: Structural characterization by SANS." Journal of Colloid and Interface Science, vol. 274, 2004, pp. 251-267.
Delgado-Charro et al., "Delivery of a hydrophilic solute through the skin from novel microemulsion systems," Eur. J. Pharmaceutics and Biopharmaceutics, 43(1 ):37-42, 1997.
Hickerson et al., SiRNA-Mediated Selective Inhibition of Mutant Keratin mRNAs Responsible for the Skin Disorder Pachyonychia Congenita, Ann. N.Y. Acad. Sci., 1082:56-61 (2006).
International Search Report for Application No. PCT/US06/26918, dated Jun. 19, 2008.
International Search Report for Application No. PCT/US06/46236, dated Jun. 17, 2008.
Kakumanu, Srikanth, et al. "A Nanoemulsion Formulation of Dacarbazine Reduces Tumor Size in a Xenograft Mouse Epidermoid Carcinoma Model Compared to Dacarbazine Suspension" Nanomedicine: NBM, 7(3):277-283, 2011.
Keen et al., Botulinum toxin A for hyperkinetic facial lines: results of a double-blind, placebo-controlled study, Plastic and Reconstructive Surgery, 1994; 94(1):94-9.
Kitson, "Drugs Used for Skin Diseases," Published in Dermatologic, Cosmeceutic, and Cosmetic Development Therapeutic and Novel Approaches, Ed. Walters and Roberts, pp. 11-20 (2008).
Kuo, Fonghsu, et al. "Nanomulsions of an Anti-Oxidant Synergy Formulation Containing Gamma Tocopherol Have 1 Enhanced Bioavailability and Anti-Inflammatory Properties", International Journal of Pharmaceutics, 363, 2008, pp. 206-213.
Lin et al., Delivery of plasmid DNA expression vector for karatinocyte growth factor-1 using electroporation to improve cutaneous wound healing in a septic rat model, Wound Repair and Regeneration, 14:618-624 (2006).
Schmalfuss et al., "Modification of drug penetration into human skin using microemulsions," J. Controlled Release, 46 (3):279-285, 1997.
Tagne, Jean Bosco, et al. "Nanoemulsion Preparations of the Anticancer Drug Dacarbazine Significantly Increase Its Efficacy in Xenograft Mouse Melanoma Model", Molecular Pharmaceutics, vol. 5, No. 6, pp. 1055-1063, 2008.
Wu et al., "Topical Transfection Using Plasmid DNA in a Water-in-Oil Nanoemulsion," Int. J. Pharmceutics, 221 (1/02):23-34,2001.
Wu et al., "Topical Transport of Hydrophilic Compounds Using Water-in-Oil Nanoemusions," Int. J. Pharmaceutics, 220:63-75, 2001.

* cited by examiner

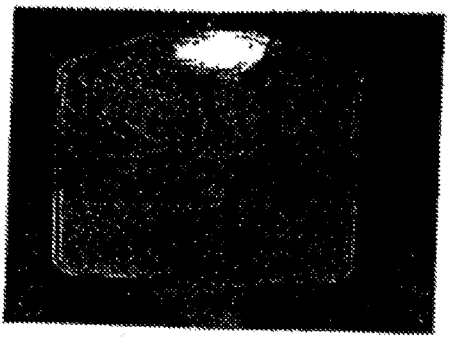
Figure 15A
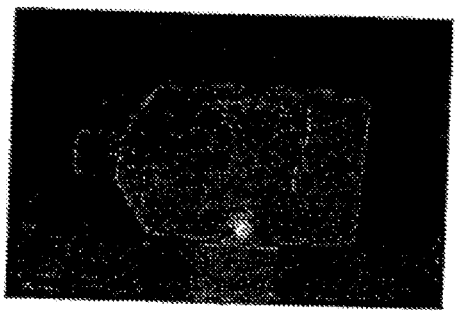
Figure 15B
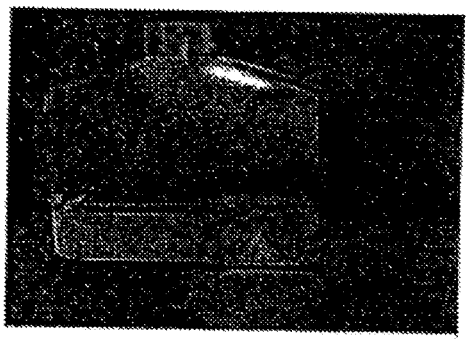
Figure 15C
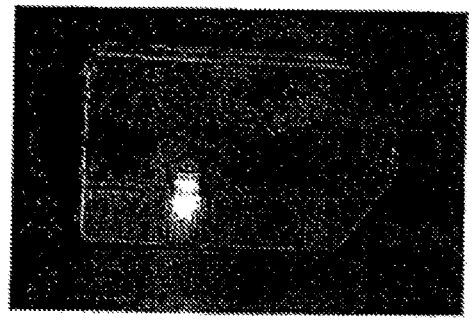
Figure 15D
Figure 15

US 10,016,364 B2

COMPOSITIONS AND METHODS FOR MAKING AND USING NANOEMULSIONS

RELATED APPLICATIONS

This application is a continuation of U.S. application Ser. No. 11/996,016, filed on Feb. 7, 2008, which is a 35 U.S.C. 371 national stage filing of International Patent Application No. PCT/US2006/026918, filed on Jul. 11, 2006, which claims priority to U.S. Provisional Patent Application No. 60/700,224 filed on Jul. 18, 2005. The entire contents of each these applications are hereby incorporated herein by reference.

FIELD OF INVENTION

The present invention relates to the field of nanoemulsions. In one embodiment, nanoemulsions are made using high shear stress technology. In one embodiment, the invention comprises uniform microfluidized nanoemulsions. In another embodiment, the uniform nanoemulsion comprises a compound such as a pharmaceutical, nutraceutical, or cosmeceutical. In one embodiment, the uniform nanoemulsion comprises improved pharmacokinetic parameters when compared to conventional nanoparticulate compositions and/or nanoemulsions. In one embodiment, the present invention contemplates a method of making a bacteria-resistant nanoemulsion.

BACKGROUND OF THE INVENTION

Micro/nanoemulsion technology has substantial commercial value. In relation to the nutraceutical area alone, the market value is estimated as a 250 billion dollar business world-wide. Consequently, the ability to incorporate lipid soluble nutraceuticals into beverages (the fastest-growing component of the food industry) as well as low or no fat foods is of important interest.

What is needed is a nanoemulsion that: i) has improved temperature and pH stability; ii) improved bioavailability; and iii) improved shelf-life due to microbial resistance. In addition, nanoemulsions should be relatively easy and inexpensive to prepare.

SUMMARY

The present invention relates to the field of nanoemulsions. In one embodiment, the nanoemulsion is made using a high shear stress technology. In one embodiment, the invention comprises uniform microfluidized nanoemulsions. In another embodiment, the uniform nanoemulsion comprises a compound such as a pharmaceutical, nutraceutical, or cosmeceutical. In one embodiment, the uniform nanoemulsion comprises improved pharmacokinetic parameters when compared to conventional nanoparticulate compositions and/or nanoemulsions. In one embodiment, the present invention contemplates a method of making a bacteria-resistant nanoemulsion.

In one embodiment, the present invention contemplates a nanoemulsion comprising a population of particles having maximum and minimum diameters, wherein the difference between said maximum and minimum diameters does not exceed 100 nm.

In one embodiment, the present invention contemplates a nanoemulsion comprising a population of particles having diameters between approximately 10 and approximately 110 nanometers, wherein said nanoemulsion is not contaminated by particles having diameters larger than 110 nanometers. In one embodiment, the particles encapsulate a compound. In one embodiment, the compound is a pharmaceutical. In another embodiment, the compound is a nutraceutical.

In one embodiment, the present invention contemplates a nanoemulsion comprising a first and second population of particles, wherein the majority of particles in said first population have diameters between approximately 10 and approximately 20 nanometers, wherein the majority of particles in said second population have diameters between approximately 40 and approximately 80 nanometers, wherein said nanoemulsion is uncontaminated by particles having diameters larger than 110 nanometers. In one embodiment, the particles encapsulate a compound. In one embodiment, the compound is a pharmaceutical. In one embodiment, the compound is a nutraceutical.

A nanoemulsion comprising a population of particles having diameters between approximately 50 and approximately 150 nanometers, wherein said nanoemulsion is not contaminated by particles having diameters larger than 160 nanometers. In one embodiment, the particles encapsulate a compound. In one embodiment, the compound is a pharmaceutical. In one embodiment, the compound is a nutraceutical.

In one embodiment, the present invention contemplates a method, comprising: a) providing; i) a premix comprising a compound and a liquid dispersion medium, wherein said compound has a solubility greater than 30 mg/ml in said medium; and ii) a microfluidizer capable of maintaining at least 25,000 PSI; b) using a single pass exposure of said premix to said microfluidizer to create a population of nanoemulsion particles having diameters ranging approximately between 10-110 nm. In one embodiment, the dispersion medium is selected from the group consisting of aqueous media and oil-based media. In one embodiment, the aqueous media is selected from the group consisting of water, ringers solution, dextrose, and short chain alcohols. In one embodiment, the oil-based media is selected from the group including, but not limited to, saturated and unsaturated oils from vegetable and marine sources, silicone oils, mineral oils, and plant-derived oils. In one embodiment, the compound is selected from the group including, but not limited to, a plant sterol, cod liver oil, tocopherol, lecithin, lutein, zeaxanthin, and soy protein.

In one embodiment, the present invention contemplates a method, comprising: a) providing; i) a heated dispersion medium; ii) a compound having substantial solubility in said medium; and iii) a microfluidizer capable of making a uniform nanoemulsion from said medium; b) adding said compound to said medium at a temperature of at least 70° C. to create a premix; and c) microfluidizing said premix at a pressure of at least 25,000 PSI to create said nanoemulsion having particle diameters ranging between 10-110 nm. In one embodiment, said dispersion medium is selected from the group consisting of soybean oil and water. In one embodiment, said dispersion medium is heated to at least 65° C. In one embodiment, said compound may be selected from the group comprising a plant sterol, cod liver oil, tocopherol, lecithin, lutein, zeaxanthin, lycopene, whey protein, and soy protein. In one embodiment, the nanoemulsion encapsulates the compound. In one embodiment, 86% of said particle diameters have a 54 nm average diameter. In one embodiment, 14% of said particles diameters have a 16 nm average diameter. In one embodiment, 82% of said particle diameters have a 64 nm average diameter. In one embodiment, 17% of said particle diameters have a 19 nm average diameter. In one embodiment, 78% of said particle diameters have a 88 nm average diameter. In one embodiment, 22% of said particle diameters have a 27 nm average diameter. In one embodiment, 84% of said particle diameters have a 90 nm average diameter. In one embodiment, 16% of said particle diameters have a 23 nm average diameter. In one embodiment, 80% of said particle diameters have a 55 nm average diameter.

In one embodiment, the present invention contemplates a method, comprising: a) providing; i) a premix comprising a compound, a first antioxidant, a second antioxidant, and an aqueous dispersion medium, wherein said compound has a solubility greater than 30 mg/ml in said medium; and iii) a microfluidizer capable of maintaining at least 25,000 PSI; c) using a single pass exposure of said premix to said microfluidizer to create a population of nanoemulsion particles having diameters ranging from between approximately 40-110 nm, wherein said particle diameter remains stable for at least four months. In one embodiment, the method further comprises pasteurizing said population of nanoemulsion particles wherein said particle diameters remain stable. In one embodiment, the method further comprises freezing said population of nanoemulsion particles wherein said particle diameters remain stable.

In one embodiment, the present invention contemplates a method, comprising: a) providing; i) a stable aqueous dispersion medium comprising a first antioxidant; ii) a solution comprising natural emulsifiers; ii) a compound having substantial solubility in said medium comprising a second antioxidant; and iii) a microfluidizer capable of making a uniform nanoemulsion from said medium; b) adding said compound and said solution to said medium and heating to a temperature of at least 50° C. to create a premix; and c) microfluidizing said premix at a pressure of at least 25,000 PSI to create said nanoemulsion having particle diameters ranging between 40-110 nm wherein said particle diameter remains stable for at least four months. In one embodiment, the nanoemulsion encapsulates the compound. In one embodiment, the method further comprises pasteurizing said nanoemulsion wherein said particle diameters remain stable.

In one embodiment, the method further comprises freezing said nanoemulsion wherein said particle diameters remain stable. In one embodiment, said solution comprises milk.

In one embodiment, said compound comprises DHA fish oil. In one embodiment, said pasteurization comprises exposing said nanoemulsions to 75° C. for thirty seconds. In one embodiment, said freezing comprises exposing said nanoemulsions to −4° C. for 24 hours.

In one embodiment, the present invention contemplates a method, comprising; a) providing; i) a subject refractory to an administered compound at a therapeutically effective amount; ii) a nanoemulsion comprising a population of particles encapsulating said compound, wherein said particles having diameters between approximately 10 and approximately 110 nanometers, wherein said nanoemulsion is not contaminated by particles having diameters larger than 110 nanometers; b) delivering said nanoemulsion to said patients under conditions such that said compound bioavailability is improved and wherein said compound is therapeutically effective.

In one embodiment, the improved bioavailability comprises pharmacokinetic parameters selected from the group consisting of decreased $T_{max}$, increased $C_{max}$, and increased AUC. In one embodiment, the delivering comprises a method selected from the group consisting of oral, transdermal, intravenous, intraperitoneal, intramuscular, and subcutaneous. In one embodiment, the nanoemulsion comprises a plant sterol. In one embodiment, the nanoemulsion comprises lycopene.

In one embodiment, the present invention contemplates a method for improving a nanoemulsion bioavailability comprising providing a uniform microfluidized nanoemulsion and delivering the uniform nanoemulsion to a subject. In one embodiment, the subject comprises a mammal. In one embodiment, the nanoemulsion encapsulates a compound. In one embodiment, the nanoemulsion is delivered by oral administration. In another embodiment, the nanoemulsion is delivered by methods including, but not limited to, transdermally, intravenously, intraperitoneally, intramuscularly or subcutaneously. In one embodiment, said improved bioavailability comprises pharmacokinetic parameters selected from the group consisting of decreased $T_{max}$, increased $C_{max}$, and increased AUC. In one embodiment, said nanoemulsion is formulated for oral administration. In one embodiment, said nanoemulsion comprises a plant sterol. In one embodiment, said nanoemulsion comprises lycopene.

In one embodiment, the present invention contemplates a nanoemulsion having bacteria-resistant properties, wherein said nanoemulsion comprises a population of particles encapsulating said compound, wherein said particles having diameters between approximately 10 and approximately 110 nanometers, wherein said nanoemulsion is not contaminated by particles having diameters larger than 110 nanometers. In one embodiment, the nanoemulsion resists bacterial growth for at least three months. In one embodiment, the bacterial-resistant properties comprise shear-force induced cell lysis. In one embodiment, the bacterial-resistant properties comprise an oxidizing environment. In one embodiment, the nanoemulsion is sterile.

In one embodiment, the present invention contemplates a uniform microfluidized nanoemulsion comprising bacteria-resistant properties. In one embodiment, said nanoemulsion resists bacterial growth for at least three months. In one embodiment, the nanoemulsion comprises particles having a diameter distribution of between 10-110 nm. In one embodiment, said bacterial-resistant properties comprise shear-force induced cell lysis. In one embodiment, the nanoemulsion is sterile.

In one embodiment, the present invention contemplates a method, comprising: a) providing; i) a premix comprising a compound and a liquid dispersion medium; and ii) a device capable of creating a continuous turbulent flow under high pressure; b) using said device to create a population of nanoemulsion particles having uniform diameter. In one embodiment, the dispersion medium is selected from the group consisting of aqueous media and oil-based media. In one embodiment, the aqueous media is selected from the group consisting of water, saline solution, ringers solution, dextrose, and short chain alcohols. In one embodiment, the oil-based media is selected from the group consisting of saturated and unsaturated oils from vegetable and marine sources, silicone oils, and mineral oils. In one embodiment, the compound is selected from the group consisting of a plant sterol, cod liver oil, tocopherol, lecithin, lutein, zeaxanthin, and soy protein.

Definitions

In general, the terms used herein are to be interpreted according to definitions generally accepted by those having ordinary skill in the art. Those listed below, however, are to be interpreted according to the following definitions.

The term "microfluidized", "microfluidizing", or "microfluidizer" as used herein refers to an instrument or a process that utilizes a continuous turbulent flow at high pressure including, but not limited to, a microfluidizer or other like device that may be useful in creating a uniform nanoemulsion. For example, microfluidizing may create a uniform nanoemulsion comprising a pharmaceutical, nutraceutical, or cosmeceutical from a premix within a thirty (30) second time frame (typically referred to a single pass exposure). Typically, a microfluidizer may be operated at a pressure of approximately 25,000 PSI to generate a uniform nanoemulsion.

The term "uniform nanoemulsion" as used herein, refers to any emulsion comprising any specified range of particle diameter sizes wherein the difference between the minimum diameter and maximum diameters do not exceed approximately 600 nm, preferably approximately 300 nm, more preferably approximately 200 nm, but most preferably approximately 100 nm (i.e., for example, microfluidization, as contemplated herein, produces a uniform nanoemulsion having a range of approximately 10-110 nm and is referred to herein as a uniform microfluidized nanoemulsion). Preferably, the total particle distribution (i.e., 100%) is encompassed within the specified range of particle diameter size. A particle diameter distribution where less than 3% is outside the specified range of particle diameter sizes is still contemplated herein as a uniform nanoemulsion.

The term "population" as used herein, refers to any mixture of nanoemulsion particles having a distribution in diameter size. For example, a population of nanoemulsion particles may range is particle diameter from between approximately 10-110 nm.

The term "nanoparticle" as used herein, refers to any particle having a diameter of less than 300 nanometers (nm), as defined by the National Science Foundation or preferably less than 100 nm, as defined by the National Institutes of Health. Most conventional techniques create nanoparticle compositions with an average particle diameter of approximately 300 nanometers (nm) or greater.

The term "dispersion medium" as used herein, refers to any oil-based or aqueous liquid wherein a pharmaceutical, nutraceutical, or cosmeceutical may be dissolved upon heating. Oil-based liquids may include, but not limited to; saturated and unsaturated oils from vegetable and marine sources including, but not limited to, soybeans, safflowers, olives, corn, cottonseeds, linseed, safflower, palm, peanuts, flaxseeds, sunflowers, rice bran, sesame, rapeseed, cocoa butter etc., and mixtures thereof; silicone oils; and mineral oils. Alternatively, aqueous media may include, but are not limited to, water, saline solutions, short chain alcohols, 5% dextrose, Ringer's solutions (lactated Ringer's injection, lactated Ringer's plus 5% dextrose injection, acylated Ringer's injection), Normosol-M, Isolyte E, and the like; and synthetic and/or natural detergents having high surfactant properties, deoxycholates, cyclodextrins, chaotropic salts and ion pairing agents etc., and mixtures thereof.

The term "compound" as used herein, refers to any pharmaceutical, nutraceutical, or cosmeceutical (i.e., for example, organic chemicals, lipids, proteins, oils, vitamins, crystals, minerals etc.) that are substantially soluble in a dispersion medium.

The term "substantially soluble" as used herein, refers to any compound that dissolves into a dispersion medium to a concentration greater than 30 mg/ml. Preferably, the dispersion medium is heated while the compound is being dissolved.

The term "premix" as used herein, refers to any mixture that is subsequently used to generate a nanoparticulate composition or a uniform microfluidized nanoemulsion. Typically, premixes contain a liquid dispersion medium and a compound, and optionally, an emulsifier and/or an antioxidant.

The term "stable" as used herein, refers to any population of nanoemulsion particles whose diameters stay within the range of approximately 10-110 nm over a prolonged period of time (i.e., for example, one (1) day to twenty-four (24) months, preferably, two (2) weeks to twelve (12) months, but more preferably two (2) months to five (5) months). For example, if a population of nanoemulsion particles is subjected to prolonged storage, temperature changes, and/or pH changes whose diameters stay within a range of between approximately 10-110 nm, the nanoemulsion is stable.

The term "bacteria-resistant" as used herein refers to the lack of observable bacterial growth.

The term "sterile" as used herein refers to a nanoemulsion that contains no living bacterial cells.

The term "pharmaceutically acceptable" as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" as used herein, refers to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The term "therapeutically effective amount" as used herein, with respect to a drug dosage, shall mean that dosage that provides the specific pharmacological response for which the drug is administered or delivered to a significant number of subjects in need of such treatment. It is emphasized that 'therapeutically effective amount,' administered to a particular subject in a particular instance will not always be effective in treating the diseases described herein, even though such dosage is deemed a "therapeutically effective amount" by those skilled in the art. Specific subjects may, in fact, be "refractory" to a "therapeutically effective amount". For example, a refractory subject may have a low bioavailability such that clinical efficacy is not obtainable. It is to be further understood that drug dosages are, in particular instances, measured as oral dosages, or with reference to drug levels as measured in blood.

The term "refractory" as used herein, refers to any subject that does not respond with an expected clinical efficacy following the delivery of a compound as normally observed by practicing medical personnel.

The term "delivering" or "administering" as used herein, refers to any route for providing a pharmaceutical or a nutraceutical to a subject as accepted as standard by the medical community. For example, the present invention contemplates routes of delivering or administering that include, but are not limited to, oral, transdermal, intravenous, intraperitoneal, intramuscular, or subcutaneous.

The term "subject" as used herein, refers to any animal to which an embodiment of the present invention may be delivered or administered. For example, a subject may be a human, dog, cat, cow, pig, horse, mouse, rat, gerbil, hamster etc.

The term "encapsulate", "encapsulated", or "encapsulating" refers to any compound that is completely surrounded by a protective material. For example, a compound may become encapsulated by a population of nanoemulsion particle formation during microfluidization.

The term "nutraceutical" refers to any compound added to a dietary source (i.e., for example, a fortified food or a dietary supplement) that provides health or medical benefits in addition to its basic nutritional value.

The term "cosmeceutical" refers to any compound (i.e., for example, benzoyl peroxide or retinol) added to a preparation that possesses both cosmetic and pharmaceutical properties. A cosmecuetical is generally useful for external applications to improve the complexion or overall physical appearance. Cosmeceuticals may be applied as compositions including, but not limited to, a cream, oil, foam, spray, liquid etc. Cosmeceuticals may include categories such as, but not limited to, carotenoids, phenolic compounds, or water soluble antioxidants.

BRIEF DESCRIPTION OF THE FIGURES

FIGS. 15A, 15B, 15C, and 15D present one embodiment of an anti-bacterial property generated during the preparation of a microfluidized plant sterol nanoemulsion.

FIGS. 18A and 18B present exemplary data comparing premix cholesterol particle diameter distributions from: FIG. 18A: Tween® 80/Water as per the '118 patent; and FIG. 18B: Oil/Lecithin/Tween® 80/Water as contemplated by one embodiment of the present invention.

FIGS. 19A and 19B present exemplary data comparing microfluidized cholesterol nanoemulsion particle diameter distributions from: FIG. 19A: Tween® 80/Water as per the '118 patent using repeated microfluidization passes; and FIG. 19B: Oil/Lecithin/Tween® 80/Water as contemplated by one embodiment of the present invention using a single microfluidization pass.

FIGS. 20A and 20B present exemplary data comparing microfluidized cholesterol nanoemulsion particle diameter distributions from: FIG. 20A: Tween® 80/Water as per the '118 patent using a single pass exposure; and FIG. 20B: Oil/Lecithin/Tween® 80/Water as contemplated by one embodiment of the present invention using a single pass exposure.

DETAILED DESCRIPTION OF THE INVENTION

Figure 1A:
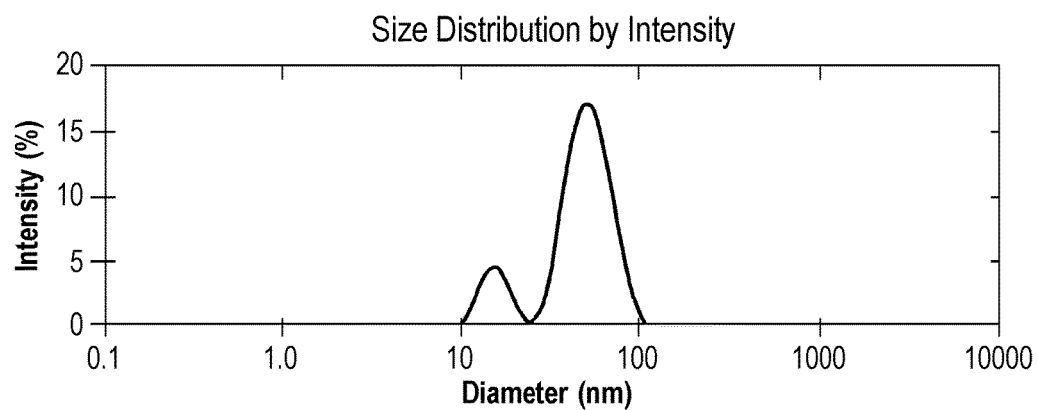
FIG. 1A presents exemplary data showing the particle diameter distribution of a microfluidized plant sterol nanoemulsion population three (3) months after preparation.

The present invention relates to the field of nanoemulsions. In one embodiment, the nanoemulsion is created by a high shear stress technology. In one embodiment, the invention comprises uniform microfluidized nanoemulsions. In another embodiment, the uniform nanoemulsion comprises a compound such as a pharmaceutical, nutraceutical, or cosmeceutical. In one embodiment, the uniform nanoemulsion comprises improved pharmacokinetic parameters when compared to conventional nanoparticulate compositions and/or nanoemulsions. In one embodiment, the present invention contemplates a method of making a bacteria-resistant nanoemulsion.

The use of nanoemulsions as a delivery system is generally directed to Pharmaceuticals. Nanoemulsion nutraceutical delivery, however, has received little attention. For example, one nanoemulsion system contains plant sterols. Bruce et al., "Method for producing dispersible sterol and stanol compounds" U.S. Pat. No. 6,387,411 (2002)(herein incorporated by reference). This technology, however, uses a grinding method to produce the nanoemulsions, and consequently, the particle diameter is at least six (6) times greater than contemplated herein. Although it is not necessary to understand the mechanism of an invention, it is believed that this diameter difference offers particular advantages in stability and efficacy (infra). Further, the '411 patent does not disclose the incorporation of absorbable micronutrients.

A further use of nanoemulsions as a delivery system is directed to cosmeceuticals. Cosmeceuticals may comprise, for example; carotenoids including, but not limited to, a-carotene, P-carotene, P-cryptoxanthin, lycoperie, crocetin, fucoxanthin, halocynthiaxanthin, canthaxanthin, astraxanthin, lutein, or zeaxanthin; phenolic compounds including, but not limited to, quercetin, rutin, myricetin, kaemferol, catechin, epigallocatechin, epicatechin, reservatrol, tocopherol, ferulate, ubiquinol-10, soy isoflavones such as genestein, daidzein, alpha lipoic acid, anthocyanins, ellagic tannins, gallic or ellagic acids; or water soluble antioxidants such as ascorbic acid, uric acid, or bilirubin.

The present invention is directed to populations of nanoparticles or nanoemulsions comprising an oral delivery vehicle for all absorbable (i.e., for example, fat-soluble) nutrients including, but not limited to, fatty acids, carotenoids, tocopherols, tocotrienols, and coenzyme-Q. Delivery methods, however, are not limited to oral and include, but are not limited to, transdermal, intravenous, intraperitoneal, intramuscular, or subcutaneous. In another embodiment, the carotenoids include, but are not limited to, lutein and zeaxanthin. The present invention is also directed to populations of nanoparticles or nanoemulsions comprising an oral delivery vehicle for all non-absorbable (i.e., for example, fat soluble) plant sterol compounds including, but not limited to, phytosterols and phytostanols. In one embodiment, the compounds are encapsulated by the nanoparticles or nanoemulsions. In one embodiment, common emulsifying agents are used to prepare the nanoemulsions. In one embodiment, the emulsifying agents include, but are not limited to, phospholipids, fatty acid monoglycerides, fatty acid diglycerides, or polysorbates.

The present invention also contemplates that certain nanoemulsion embodiments of the present invention comprise a surface-to-volume ratio that results in an improved bioavailability over current methods and compositions known in the art.

The present invention also contemplates that certain nanoemulsion embodiments of the present invention are resistant to microbiological growth. Although it is not necessary to understand the mechanism of an invention, it is believed that the microfluidization process comprises a high sheer stress and/or creates an oxidizing environment, thereby disrupting microbial integrity and/or preventing microbial growth.

I. Methods of Making Nanoemulsions

Nanoemulsions have been generated by a variety of methods. In particular, these methods provide a wide variation in particle diameter and require organic solvents and or polymers. When these known nanoemulsions are considered for an oral drug or nutrient delivery system, issues of biocompatibility and physiological side effects become an important issue.

In one embodiment, the present invention contemplates a method of making a nanoemulsion comprising a continuous turbulent flow at high pressure. In one embodiment, the high pressure turbulent flow comprises microfluidization. In one embodiment, a uniform nanoemulsion is generated from a premix using a single pass exposure (i.e., for example, within a thirty (30) second time frame). In one embodiment, the uniform nanoemulsion comprises a population of particles whose difference between the minimum and maximum diameters does not exceed approximately 100 nm, In one embodiment, a uniform nanoemulsion is generated using a pressure of at least 25,000 PSI. In one embodiment, the present invention contemplates a method of making uniform microfluidized nanoemulsions without organic solvents or polymers. In one embodiment, the microfluidized nanoemulsion is made from a suspension. In another embodiment, the microfluidized nanoemulsion is made from a microemulsion.

In one embodiment, the present invention contemplates a uniform microfluidized nanoemulsion using compounds that are substantially soluble in a liquid dispersion medium. In one embodiment, the nanoemulsion encapsulated the compounds. In one embodiment, the compounds comprise Pharmaceuticals and/or nutraceuticals. Exemplary nutraceuticals and dietary supplements are disclosed, for example, in Roberts et al., Nutriceuticals: The Complete Encyclopedia of Supplements, Herbs, Vitamins, and Healing Foods (American Nutriceutical Association, 2001), which is specifically incorporated by reference. Dietary supplements and nutraceuticals are also disclosed in Physicians' Desk Reference for Nutritional Supplements, 1st Ed. (2001) and The Physicians' Desk Reference for Herbal Medicines, 1st Ed. (2001), both of which are also incorporated by reference. A nutraceutical or dietary supplement, also known as a phytochemical or functional food, is generally any one of a class of dietary supplements, vitamins, minerals, herbs, or healing foods that have medical or biological effects on the body.

Exemplary nutraceuticals or dietary supplements include, but are not limited to, lutein, folic acid, fatty acids (e.g., DHA and ARA), fruit and vegetable extracts, vitamin and mineral supplements, phosphatidylserine, lipoic acid, melatonin, glucosamine/chondroitin, Aloe Vera, Guggul, amino acids (e.g., glutamine, arginine, iso-leucine, leucine, lysine, methionine, phenylalanine, threonine, tryptophan, and valine), green tea, lycopene, whole foods, food additives, herbs, phytonutrients, antioxidants, flavonoid constituents of fruits, evening primrose oil, flax seeds, fish and marine animal oils, and probiotics. Nutraceuticals and dietary supplements also include bio-engineered foods genetically engineered to have a desired property, also known as "pharmafoods."

In particular, these compounds include, but are not limited to, naturally occurring oils, fatty acids, and proteins. In one embodiment, a naturally occurring oil comprises fish oil (i.e., for example, cod liver oil). In one embodiment, a naturally occurring fatty acid comprises an omega-3 (i.e., for example, DHA). In one embodiment, the nanoemulsion comprises little or no fat. In one embodiment, a naturally occurring protein comprises soy or whey.

In one embodiment, the present invention contemplates a method of making a uniform microfluidized nanoemulsion comprising a population of particles whose diameter ranges from between 10-110 nm.

A. The Microfluidizer

Microfluidization is a unique process that powers a single acting intensifier pump. The intensifier pump amplifies the hydraulic pressure to the selected level which, in turn, imparts that pressure to the product stream. As the pump travels through its pressure stroke, it drives the product at constant pressure through the interaction chamber. Within the interaction chamber are specially designed fixed-geometry microchannels through which the product stream will accelerate to high velocities, creating high shear and impact forces that generates a uniform nanoemulsion as the high velocity product stream impinges on itself and on wear-resistant surfaces.

As the intensifier pump completes its pressure stroke, it reverses direction and draws in a new volume of product. At the end of the intake stroke, it again reverses direction and drives the product at constant pressures, thereby repeating the process.

Upon exiting the interaction chamber, the product flows through an onboard heat exchanger which regulates the product to a desired temperature. At this point, the product may be recirculated through the system for further processing or directed externally to the next step in the process. Cook et al., "Apparatus For Forming Emulsions" U.S. Pat. No. 4,533,254 (1985); and Cook et al., "Method Of Forming A Microemulsion" U.S. Pat. No. 4,908,154 (1990)(both herein incorporated by reference).

B. Nanoparticulate Compositions

Early attempts using microfluidizers to create nanoparticulate compositions required drug substances that were poorly soluble in a liquid dispersion medium. In one disclosed technology, "poorly soluble" was defined as less than 10 mg/ml. Bosch et al., "Process for preparing therapeutic compositions containing nanoparticles" U.S. Pat. No. 5,510,118 (1996)(herein incorporated by reference). While water-insolubility was preferably considered, oil-insoluble compounds were also subjected to a microfluidization process. The '118 patent's microfluidization process is described as a "milling" action, thus indicating that the insoluble compound particles are undergoing a physical disintegration during the creation of the nanoparticulate composition. Further, this previous process requires long-processing times (i.e., repeated microemulsifying cycles) thereby promoting heat build-up in the microfluidizer. Consequently, this early technique requires processing temperatures of less than 40° C. One problem is that this technique resulted in average nanoemulsion particle diameters of approximately 300 nm.

Despite teachings within the M18 patent that lower particle diameters (i.e., less than 100 nm) can be achieved, no data is presented demonstrating such a capability. Exemplary data presented herein has used the Bosch et al. process to produce a complete particle diameter distribution profile. See Example 13. These data show that the Bosch et al. technology cannot produce a uniform nanoemulsion as contemplated by the present invention.

Several others have implemented the basic '118 technology to encapsulate various insoluble compounds. In fact, these subsequent disclosures define a nanoparticle composition as "particles consisting of a poorly soluble therapeutic or diagnostic agent having adsorbed onto, or associated with, the surface thereof a non-crosslinked surface stabilizer". Cooper et al., "Nanoparticulate Sterol Formulations And Novel Sterol Combinations" United States Patent Application Publication No. 2004/0033202 A1 (2004)(see pg 1 para 3)(herein incorporated by reference). Like the '118 patent, Cooper et al. discloses preparing nanoparticulate compositions using compounds that are poorly soluble in a liquid dispersion medium (i.e., water, oils, alcohols, glycols, etc.). For example, Cooper et ah defines a "poorly water-soluble" drug as having a solubility of less than about 30 mg/ml. For example, plant sterol nanoparticulate compositions comprising one or more sterols or stanols (i.e., sitosterol or phytosterols) are suggested in the art as having a particle diameter of less than 50 nm. Cooper et al. does not use a microfluidizer nor present any data showing a capability of providing a uniform particle diameter ranging between 10-110 nm. Instead, Cooper et al. relies upon a more traditional milling process that does not produce a uniform particle diameter distribution ranging between 10-110 nm.

Cooper et al. employs a milling grinder known in the art as a DYNO®-MILL KDL. This equipment is currently marketed in the United States by Glen Mills, Inc. (Clifton, N.J.) and advertises with the following technical information. The DYNO®-MILL is a versatile horizontal bead mill having applications ranging from paints and coatings to drug manufacturing and cell disruption for extracting proteins. Grinding to a mean diameter of 320 nm has been reported in research papers. Operation of the DYNO®-MILL is always wet, that is, the material to be ground is held in suspension in any suitable liquid. A jacketed grinding chamber contains a series of agitators that are equally spaced along the length of a central shaft. The jacket on the grinding chamber is used to control the temperature of the material being processed. The chamber is secured at one end and cantilevers out over the shaft. The bearing end contains a separator gap which has clearance tolerances that can be set as tight as 20 microns. The chamber is filled to about 80% of its capacity with beads (i.e., PolyMill® 500; 500 μm diameter grinding beads). Depending on the specific application beads made from glass, ceramic, metals, tungsten carbide and other materials are available. The process material is now introduced into the chamber. When the chamber is full of material and beads, the machine is switched on and the agitator discs rotate forcing the beads to impact over and over with the process material with hurricane-like force. This action of having thousands of separate impacts produces rapid and consistent size reduction. Batch and continuous processing can be handled in the same mill by changing the grinding chamber and the gap setting.

At best, Cooper et ah is limited to a plant sterol nanoparticulate composition where 90% of the particle diameters are below 187 nm. The actual particle diameter distribution, however, is not presented. In one embodiment, the present invention contemplates that the technology described by Cooper et al cannot produce a uniform particle diameter distribution ranging between 10-110 nm. See Example 14. Unlike some embodiments of the present invention, Cooper et al. has not considered methods to make a nanoparticulate composition that include a heating process. In fact, Cooper et al. presents a discussion concluding that preparing a plant sterol nanoparticulate composition using a process that includes heating is not desirable and problematic. Some embodiments of the present invention have solved those problems.

Two drugs that are insoluble in a selected liquid dispersion medium, meloxicam and topiramate, are suggested as potential candidates for improved clinical administration using the Cooper et al. nanoparticulate composition technology. Cooper et al., "Nanoparticulate meloxicam formulations" US Pat. Appln Publ No. 2004/0229038 (2004); and Gustow et al., "Nanoparticulate topiramate formulations" US Pat. Appln Publ No. 2004/0258758 (2004). Neither publication contains any exemplary data demonstrating the creation of a uniform microfluidized microemulsion having a particle diameter range of about 10-110 nm.

C. Nanoemulsification

The formation of a uniform mixture (i.e., for example, a population) of predominantly small particles may involve a physical process termed "emulsification".

An emulsion is traditionally defined in the art "as a system . . . consisting of a liquid dispersed with or without an emulsifier in an immiscible liquid usually in droplets of larger than colloidal size" *Medline Plus Online Medical Dictionary*, Merriam Webster (2005). Consequently, as the art developed emulsifiers capable of generating smaller and smaller diameter particles, the terms "microemulsion" and "nanoemulsion" became known. Conceptually, a microemulsion is one thousand-fold greater in diameter than a nanoemulsion. However, particle diameter distributions may vary widely in a non-controlled emulsification process creating considerable overlap between the nanoemulsion and microemulsion technologies.

In one embodiment, the present invention contemplates a premix comprising a compound substantially soluble (i.e., for example, greater than 30 mg/ml) in a liquid dispersion medium (i.e., for example, a heated liquid dispersion medium) and, optionally, common emulsifying agents including, but not limited to, phospholipids, fatty acid monoglycerides, fatty acid diglycerides, or polysorbates. In one embodiment, a nanoemulsion is created by exposing a premix to a continuous turbulent flow at a high pressure, wherein the pressure is at least 25,000 PSI. In one embodiment, the high pressure turbulent flow comprises microfluidization. In one embodiment, the nanoemulsion comprises particles encapsulating pharmaceuticals or nutraceuticals. In one embodiment, the nanoemulsion comprises a uniform nanoemulsion having stable particles. In one embodiment, the microfluidization comprises a single pass exposure (i.e., for example, approximately thirty (30) seconds). In one embodiment, a uniform plant sterol microfluidized nanoemulsion has an improved low density lipoprotein cholesterol lowering efficacy.

Oral drug administration is a common method for providing pharmaceuticals and nutraceuticals to any subject. The contemplated methods of delivering a nanoemulsion is not limited to oral and include, for example, transdermal, intravenous, intraperitoneal, intramuscular, or subcutaneous routes of administration. Oral administration is favored because the formulations (i.e., liquids or suspensions) are relatively inexpensive to produce and are well tolerated. Subsequent gastrointestinal absorption of the formulation's ingredients, however, is not as predictable. For the pharmaceuticals and nutraceuticals to gain entrance into the subject, the formulations must be compatible with the digestive system. Consequently, lipid-based drug delivery systems are known to be useful as carriers for many drug delivery systems. Their efficacy, however, may be dependent upon; i) lipid composition (i.e., for example, molecular size and charge); ii) pharmaceutical, nutraceutical, or cosmeceutical chemical structure (i.e., molecular size and pH ionization); and iii) the overall health of the subject. Lipids are generally categorized as physiologically non-absorbable or absorbable. It should be recognized that gastrointestinal absorption processes are unrelated to a compound's solubility properties. The present invention contemplates compositions and methods related to uniform microfluidized nanoemulsions comprising either absorbable or non-absorbable lipids thereby improving their bioavailability.

1. Non-Absorbable Lipids

Plant sterols, stanols, and triterpene alcohols (i.e., for example, oryzanol) are either not absorbed, or poorly absorbed, into the bloodstream following oral administration. In one embodiment, the present invention contemplates a method of making a uniform nanoemulsion (i.e., for example, microfluidized) comprising a non-absorbable lipid having substantial solubility in a liquid dispersion medium and, optionally, common emulsifying agents, such as phospholipids, fatty acid monoglycerides, fatty acid diglycerides, or polysorbates to formulate improved nanoemulsions. In one embodiment, the nanoemulsion comprises particle diameters ranging between 10-110 nm, thereby improving oral administration.

The use of plant sterols, such as p-sitosterol, is known to reduce blood cholesterol levels because it is non-absorbable. The presence of unabsorbed plant sterols in the gastrointestinal system inhibits the normal metabolism of cholesterol and, concomitantly, decreases blood cholesterol levels. Specifically, administration of twenty (20) gms of crystalline plant sterols can reduce plasma cholesterol levels approximately 10%. Pollack et al., "Sitosterol", *In: Monographs on Atherosclerosis*, Vol. 10, Eds. O. J. Pollack & D. Kritchevsky, Basel, N.Y., Karger (1981).

Further, non-absorbable lipids are advantageous as a nutraceutical because of a lack of side effects. Side effects are routinely observed when using traditional pharmaceutical systemic cholesterol-lowering interventions (i.e., for example, HMG Co A reductase inhibitors or niacin). Because of the very low incidence of side effects, plant sterols can be prescribed for the general population, including children for whom systemic interventions are rarely recommended. It is known that the consumption of adequate amounts of plant sterols will lower blood cholesterol levels. The present invention contemplates improvements in currently known methods to deliver plant sterols or stanols.

The first known method involves dissolving the plant sterol in a vegetable oil-containing margarine to an efficacious level of plant sterol. When the fat solubility of a free stanol or a sterol is increased by: i) interesterified with a fatty acid such oleate or linoleate; ii) mixed in vegetable oil; or iii) hydrogenated to produce margarine, plasma cholesterol can be reduced by approximately 30%. To ingest enough plant sterol, this process can result in the consumption of up to approximately eighteen (18) grams of fat. Miettinen et al., "Use of a stanol fatty acid ester for reducing serum cholesterol level" U.S. Pat. No. 5,502,045 (1996); and Wester et al., "Phytosterol compositions" U.S. Pat. No. 6,589,588 (2003)(both herein incorporated by reference). To fat conscious Americans, coupled with the high cost of the margarines, this is unacceptable for a naturopathic approach to lower plasma cholesterol. A disadvantage of this method is that overweight or obese people frequently have elevated cholesterol levels. Physicians, of course, caution this subject group to avoid additional dietary fat. In one embodiment, the present invention contemplates a method of making a beverage nanoemulsion that comprises plant sterols. For example, the method to make the beverage nanoemulsion may comprise a continuous turbulent flow at a high pressure. In one embodiment, the continuous turbulent high pressure flow comprises microfluidization. In another embodiment, the nanoemulsion beverage comprises an orange juice product.

The second known method comprises oral delivery of water-dispersible plant sterols (i.e., for example, a stanol not dissolved in fat) by incorporation micron-sized micelles (i.e., microemulsions having diameters of several thousand nanometers) which can be subsequently added to beverages or foods. Ostlund, Jr., "Sitostanol formulation to reduce cholesterol absorption and method for preparing and use of same" U.S. Pat. No. 5,932,562 (1999)(herein incorporated by reference). When the microemulsion containing the plant sterol was administered into the intestine, cholesterol absorption was reduced by approximately 37%. Ostlund, Jri, "Sitostanol formulation to reduce cholesterol absorption and method for preparing and use of same" U.S. Pat. No. 5,932,562 (1999)(herein incorporated by reference); and Spillburg et al., "Fat-free foods supplemented with soy stanol-lecithin powder reduce cholesterol absorption and LDL cholesterol" *J Am Diet Assoc.* 103:577-581 (2003). A disadvantage of this method is that the particle diameters of these microemulsion preparations are on the order of thousands of nanometers (i.e., micron diameters) and thereby does not provide optimal efficacy. The present invention contemplates a nanoemulsion technology comprising a specific formulation and a microfluidization process that provides particle diameters from between 10-110 nm. In one embodiment, the nanoparticle has improved pH and temperature stability properties, thereby stabilizing the particle's integrity throughout the gastrointestinal system.

The third known method involves the oral delivery of plant sterols by producing a water dispersible sterol product. These water dispersible products usually include emulsifying agents including, but not limited to, monoglycerides and polysorbates. These water dispersible products are known to be homogenized using a liquid/liquid dispersion having particle diameters less than 1000 nm (mean=358 nm). The present invention, however, contemplates a microfluidizing nanoemulsion technology (i.e., for example, that produced by a continuous flow high pressure process) that improves the emulsification of these water-dispersible plant sterols into nanoemulsions having a particle diameter of approximately 40-60 nm.

Similarly, methods are known for preparing water dispersible sterol/stanol or sterol/stanol ester compositions by co-melting the stanol/sterols with highly branched hydrocarbons and then grinding the resulting product. Bruce et al., "Method for producing dispersible sterol and stanol compounds" U.S. Pat. No. 6,387,411 (2002)(herein incorporated by reference). This grinding method typically produces particle diameters ranging from 10-150 microns. Other methods known to produce a water dispersible sterol product use homogenization in emulsifying agents including, but not limited to, monoglycerides and polysorbates. These homogenization procedures have been reported to produce a liquid/liquid dispersion with a particle diameter less than 1000 nm (mean=358 nm). Stevens et al., "Aqueous dispersible sterol product" U.S. Pat. No. 6,623,780 (2003)(herein incorporated by reference). This preparation, when added to orange juice, can reduce LDL cholesterol by approximately 12%. Devaraj et al, "Plant sterol-fortified orange juice effectively lowers cholesterol levels in mildly hypercholesterolemic healthy individuals" *Arterioscler Thromb Vase Biol* 24:25-28 (2004).

Although it is not necessary to understand the mechanism of an invention, it is believed that a much greater surface-to-volume ratio is reached in the uniform microfluidized nanoemulsion preparations made according to the present invention (i.e., for example, up to 6 fold) and results in greater stability. Consequently, it is further believed that, any incorporated pharmaceutical, nutraceutical, or cosmeceutical has improved efficacy (i.e., for example, plasma cholesterol lowering by a plant sterol). It is further believed that a smaller-sized plant sterol-containing nanoparticles contemplated by one embodiment of the present invention, when compared to known micron-sized micelles or microemulsions, has an improved disruption of the normal micellar delivery of dietary cholesterol to the digestive tract. For example, it is known that pre-formed micron-size micelles containing plant stanols were up to three (3) times more efficacious in inhibiting cholesterol absorption than a suspension of crystalline stanot. Ostlund et al., "Sitostanol administered in lecithin micelles potently reduces cholesterol absorption in humans" *Am J Clin Nutr* 70:826-831 (1999).

2. Absorbable Lipids

This invention also relates to the use of nanoemulsions as an oral delivery vehicle for absorbable lipids including, but not limited to, fatty acids, carotenoids, tocopherols, and other fat soluble vitamins, tocotrienols, and Coenzyme-Q. In one embodiment, the present invention contemplates a method to make a uniform microfluidized nanoemulsion comprising an absorbable lipid having substantial solubility in a liquid dispersion medium and, optionally, common emulsifying agents, such as phospholipids, fatty acid monoglycerides, fatty acid diglycerides, or polysorbates to formulate improved nanoemulsions. In one embodiment, the method comprises a step exposing a premix to a continuous turbulent flow at high pressure. In one embodiment, the pressure is at least 25,000 PSI. In one embodiment, the nanoemulsion comprises carotenoids, including, but not limited to, lutein and zeaxanthin. In one embodiment, the nanoemulsion comprises nanoparticles having a particle diameter ranging from 10-110 nm, thereby improving bioavailability. In one embodiment, nanoemulsion bioavailability is improved following oral, transdermal, intravenous, intraperitoneal, intramuscular or subcutaneous delivery.

In one embodiment, the present invention contemplates a method to treat or prevent macular degeneration (i.e., a major cause of blindness in people of 65) providing an improved nanoemulsion comprising at least one carotenoid. In one embodiment, the carotenoid is selected from the group comprising lutein or zeaxanthin.

Under normal physiological conditions these types of compounds may be poorly absorbed by the gastrointestinal system. Consequently predicable lipid nutrient absorption is highly variable thus resulting in a highly variable lipid bioavailability (i.e., for example, the percentage, of the dose absorbed). Factors influencing bioavailability may include, but are not limited to, food processing methods, food matrix, and physiological solubility in naturally-occurring micelles (i.e., for example, the lipid micellular transport system).

Fat-soluble nutrients can be incorporated into high fat-containing vegetable oils for dispersal into a fat matrix (i.e., for example a micron-sized micelle). The micelle solubilizes the lipid-soluble nutrient thereby allowing absorption by the small intestine. For example, when plant sterols are delivered in a micelle, cholesterol absorption inhibition is increased up to three-fold. Ostlund et al., "Sitostanol administered in lecithin micelles potently reduces cholesterol absorption in humans" *Am J Clin Nutr* 70:826-831(1999).

Similarly, an increased in vitro carotenoid bioavailability in cell cultures is observed when solubilizing the carotenoids in micelles. Xu et al., "Solubilization and stabilization of carotenoids using micelles: delivery of lycopeneto cells in culture" *Lipids* 34:1031-1036 (1999). A disadvantage of using micelles, however, involves the use of chlorinated organic solvents, a practice that should be avoided in the processing of foods stuffs. Another in vitro experiment demonstrates that a nanoemulsion preparation of lipophilic substances, such as fatty acids, vitamins, and beta-carotene can be delivered into cell culture medium (RPMI-1640) and incorporated by TK-6 cells. Zuelli et al., "Delivering lipophilic substances into cells using nanoemulsions" U.S. Pat. No. 6,558,941 (2003) (herein incorporated by reference).

II. Uniform Nanoemulsion Pharmacokinetics

In one embodiment, the present invention contemplates a nanoemulsion produced by a continuous turbulent flow at high pressure having improved pharmacokinetic properties when compared to conventional nanoparticulate compositions and/or nanoemulsions currently known in the art. It is known that nanoparticles deliver and/or release drugs (i.e., for example, norflaxin) and/or proteins (i.e., for example, serum albumin) more effectively than microparticles. Jeon et al., "Effect of solvent on the preparation of surfactant-free poly(DL-lactide-co-glycolide) nanoparticles and norfloxacin release characteristics* *Int J Pharm* 207; 99-108(2000); and Panyam et al., "Polymer degradation and in vitro release of a model protein from poly(D,L-lactide-co-glycolide) nano- and microparticles" *J Control Release* 92:173-187 (2003).

One embodiment of the present invention contemplates a uniform microfluidized nanoemulsion having improved pharmacokinetic properties when compared to conventional nanoparticulate compositions and/or nanoemulsions currently known in the art. One advantage of uniform microfluidized nanoemulsions comprises a narrow particle diameter range (i.e., for example, 10-110 nm). Most conventional nanoparticle compositions and/or nanoemulsions currently known have a wide distribution of particle diameters that interfere with the improved efficacies and bioavailabilities of the smaller sized particles.

The present invention has solved the problem of generating nanoemulsions with highly variable particle diameters and provides a more uniformly small-sized nanoemulsions (i.e., for example, a uniform nanoemulsion comprising stable particles). Consequently, these uniform nanoemulsions provide improved pharmacokinetic parameters when compared to conventional nanoparticle compositions and/or nanoemulsions currently known in the art independent of the mode of delivery which includes, but is not limited to, oral, transdermal, intravenous, intraperitoneal, intramuscular, subcutaneous, etc.

A. Absorption Phase

The use of conventional nanoparticulate compositions or nanoemulsions is not ideal due to delayed onset of action. In contrast, a uniform microfluidized nanoemulsion as contemplated by the present invention exhibits faster therapeutic effects.

Pharmaceuticals and nutraceuticals are commercially available as tablets, liquids, gel caps, capsules etc., generally intended for oral administration. Peak plasma concentrations of these compositions usually occur between 2-4 hours following administration.

When a uniform microfluidized nanoemulsion contemplated by the present invention is formulated into an oral dosage form peak plasma concentrations of an incorporated compound can be obtained in less than about 2 hours, preferably less than about 1 hour, more preferably less than about 30 minutes, but most preferably between 1 and 15 minutes.

B. Frequency of Dosing and Dosage Quantity

The recommended total daily dose of most Pharmaceuticals and nutraceuticals are administered in divided doses. It is known in the art that a single daily dose may be preferable to multiple dose each day. For example, in studies of adults with partial onset seizures, a daily dose of 200 mg/day has inconsistent effects and is less effective than 400 mg/day. See Physicians' Desk Reference, 57.sup.th Edition, pp. 2502 (2003).

In contrast, some uniform microfluidized nanoemulsions of the present invention may be administered less frequently, at lower doses, and in dosage forms such as liquid dispersions, powders, sprays, solid re-dispersible dosage forms, ointments, creams, etc.

Exemplary types of formulations useful in the present invention include, but are not limited to, liquid dispersions, gels, aerosols (pulmonary and nasal), ointments, creams, solid dose forms, etc. of any pharmaceutical, nutraceutical, or cosmeceutical. Lower dosages can be used because the smaller particle diameters of embodiments of the present invention ensure more complete absorption.

In one embodiment, the present invention contemplates a therapeutically effective amount of a uniform microfluidized nanoemulsion having $\frac{1}{6}$, $\frac{1}{5}$, $\frac{1}{4}$, $\frac{1}{3}$, or $\frac{1}{2}$ of the therapeutically effective amount of a conventional pharmaceutical, nutraceutical, or cosmeceutical formulations.

C. Oral Administration

A liquid dosage form of a conventional nanoparticulate or nanoemulsion composition would be expected to be a relatively large volume, highly viscous substance which would not be well accepted by subject populations. Moreover, viscous solutions can be problematic in parenteral administration because these solutions require a slow syringe push and can stick to tubing. In addition, conventional formulations of poorly water-soluble active agents tend to be unsafe for intravenous administration techniques, which are used primarily in conjunction with highly water-soluble substances. Embodiment contemplated by the present invention solves this problem by utilizing a liquid dispersion medium in which the pharmaceutical, nutraceutical, or cosmeceutical is substantially soluble.

Liquid dosage forms of embodiments of a uniform microfluidized nanoemulsion provide significant advantages over a liquid dosage form of a conventional nanoparticulate or nanoemulsion. In one embodiment, the uniform microfluidized nanoemulsion comprises a low viscosity. In another embodiment, the uniform nanoemulsion comprises a silky texture. These advantages include, for example: i) better subject compliance due to the perception of a lighter formulation which is easier to consume and digest; ii) ease of dispensing because one can use a cup or a syringe; iii) potential for formulating a higher concentration of a pharmaceutical, nutraceutical, or cosmeceutical resulting in a smaller dosage volume and thus less volume for the subject to consume; and iv) easier overall formulation concerns.

Liquid formulations of uniform nanoemulsions contemplated by the present invention are easier to consume which is especially important when considering juvenile subjects, terminally ill subjects, and elderly subjects. Viscous or gritty formulations, and those that require a relatively large dosage volume, are not well tolerated by these subject populations. Liquid oral dosage forms can be particularly preferably for subject populations who have difficulty consuming tablets, such as infants and the elderly, The viscosities of liquid dosage forms of nanoparticulate topiramate according to the invention are preferably less than about $\frac{1}{200}$, less than about $\frac{1}{175}$, less than about $\frac{1}{150}$, less than about $\frac{1}{125}$, less than about $\frac{1}{100}$, less than about $\frac{1}{75}$, less than about fraction $\frac{1}{50}$, or less than about $\frac{1}{25}$ of a liquid oral dosage form of a conventional nanoparticulate composition or nanoemulsion at about the same concentration per ml.

In one embodiment, the present invention contemplates a uniform microfluidized nanoemulsion that is not turbid. In one embodiment, turbid refers to the property of particulate matter that can be seen with the naked eye or that which can be felt as "gritty" when consumed. Embodiments of nanoemulsions contemplated by the present invention can be poured out of or extracted from a container as easily as water, whereas a liquid dosage form of a conventional nanoparticulate or nanoemulsion composition is expected to exhibit notably more "sluggish" characteristics.

D. Increased Bioavailability

In one embodiment, the present invention contemplates a uniform microfluidized nanoemulsion having an increased bioavailability and a smaller dose requirement as compared to prior conventional nanoparticulate compositions and nanoemulsions administered at the same dose.

Any pharmaceutical, nutraceutical, or cosmeceutical can have adverse side effects if administered at a specific dose for a specific duration. Thus, lower doses which can achieve the same or better therapeutic effects as those observed with larger doses are desired. Such lower doses may be realized with a uniform microfluidized nanoemulsion contemplated by the present invention due to greater bioavailability as compared to conventional nanoparticulate compositions and nanoemulsions; consequently smaller dose of Pharmaceuticals and nutraceutical are likely required to obtain the desired therapeutic effect.

For example, the relative bioavailability of pharmaceutical, nutraceutical, or cosmeceutical incorporated into a conventional nanoparticulate or nanoemulsion may be about 85% (i.e., as compared to a pure solution). In one embodiment, a uniform microfluidized nanoemulsion formulated into an oral pharmaceutical, nutraceutical, or cosmeceutical dosage form has a relative bioavailability preferably greater than about 85%. In other embodiments, the relative bioavailability is greater than about 90%, or greater than about 95%, or greater than about 98%.

E. Pharmacokinetic Profiles

The present invention also provides embodiments of uniform microfluidized nanoemulsions having incorporated Pharmaceuticals and/or nutraceuticals having improved pharmacokinetic profiles when administered to mammalian subject. In one embodiment, the improved profile is compared to conventional nanoparticulate compositions and nanoemulsions.

An improved pharmacokinetic (pK) profile according to the present invention can have several different types of attributes. In one embodiment, an improved pK profile of a uniform microfluidized nanoemulsion may produce the same pK profile as a conventional nanoparticulate composition or nanoemulsion, but at a lower dose. In another embodiment, an improved pK profile requires less frequent dosing as compared to a conventional nanoparticulate composition or nanoemulsion. In one embodiment, an improved pK profile shows a faster onset of activity and/or greater quantity of drug absorbed (i.e., greater bioavailability) than conventional nanoparticulate compositions and nanoemulsions. In another embodiment, an improved pK profile allows a more effective and/or faster titration of the subject to therapeutic plasma levels.

The present invention contemplates certain embodiments of uniform microfluidized nanoemulsions comprising an improved pharmacokinetic profile as reflected by time-to-maximum-concentration (Tmax), maximum-concentration (Cmax), and/or area-under-curve (AUC) profiles.

In one embodiment, an administered dose of a pharmaceutical, nutraceutical, or cosmeceutical incorporated into a uniform microfluidized nanoemulsion comprises a Tmax less than that of a conventional nanoparticulate composition and/or nanoemulsion, administered at the same dosage. Preferably the Tmax is less than about 99%, less than about 90%, less than about 80%, less than about 70%, less than about 60%, less than about 50%, less than about 40%, less than about 30%, less than about 25%, less than about 20%, less than about 15%, or less than about 10% of the Tmax of a conventional nanoparticulate composition and/or nanoemulsion, administered at the same dosage.

In another embodiment, an administered dose of a pharmaceutical, nutraceutical, or cosmeceutical incorporated into a uniform microfluidized nanoemulsion comprises a Cmax greater than that of a conventional nanoparticulate composition and/or nanoemulsion, administered at the same dosage. Preferably, the Cmax is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the Cmax of a conventional nanoparticulate composition and/or nanoemulsion, administered at the same dosage.

In one embodiment, an administered dose of a pharmaceutical, nutraceutical, or cosmeceutical incorporated into a uniform microfluidized nanoemulsion comprises an AUC greater than that of a conventional nanoparticulate composition and/or nanoemulsion, administered at the same dosage. Preferably, the AUC is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the AUC of a conventional nanoparticulate composition and/or nanoemulsion, administered at the same dosage.

III. Sterile Nanoemulsions

The present invention contemplates a method of making a nanoemulsion having anti-bacterial properties. In one embodiment, the method comprises a step exposing a pre-mix to a continuous turbulent flow at high pressure. In one embodiment, the anti-bacterial nanoemulsion is prepared by microfluidization. In one embodiment, the exposing comprises approximately thirty (30) seconds. In another embodiment, the exposing comprises a pressure of at least 25,000 PSI. In another embodiment, the anti-bacterial nanoemulsion comprises soy protein.

For example, a powdered soy protein preparation was added to water thus creating a suspension. Then, a first aliquot of the suspension was added to a first container (i.e., for example, a cell culture falcon flask) that served as a control. A second aliquot of the suspension was microfluidized (supra) to create a nanoemulsion. The preparation was microfluidized in accordance with Example 5. The microfluidized nanoemulsion was then added to a second container. Both containers were refrigerated immediately and observed over the next several days. The control suspensions agglomerated and grew bacteria. See FIGS. 15A and 15B. In contrast, the microfluidized nanoemulsion containing the soy protein did not agglomerate or grow bacteria. See FIGS. 15C and 15D.

Although it is not necessary to understand the mechanism of an invention, it is believed that the microfluidization sterilized the bacteria. It is further believed that the microfluidization shear stress resulted in a bacterial cell lysis thereby preventing further bacterial growth. Consequently, it is believed that microfluidization, as contemplated herein, produces a microbiologically sterile composition.

In one embodiment, the present invention contemplates a nanoemulsion comprising an oxidizing environment produced by a method comprising a continuous turbulent flow at a high pressure. In one embodiment, the nanoemulsion comprises a uniform microfluidized nanoemulsion. In one embodiment, the oxidizing environment prevents bacterial growth. In another embodiment, the oxidizing environment is bacteriocidal. In another embodiment, the oxidizing environment provides a sterile nanoemulsion.

An oxidizing nanoemulsion environment may result from an increased surface to volume ratio. In one embodiment, the present invention also contemplates a method to avoid the generation of an oxidizing environment by microfluidizing in the presence of an antioxidant. In one embodiment, the antioxidant reduces the presence of reactive oxygen species (ROS) in the microfluidized nanoemulsion. In another embodiment, the antioxidants are encapsulated by the nanoparticles for subsequent release to the subject.

TABLE 1

Oxidative Stress in Nanoemulsion Formulations As Measured By Malondialdehyde Formation

| Formulation | Sample 1 | Sample 2 | Sample 3 | Mean |
|---|---|---|---|---|
| Plasma (unoxidized control) | 4.0 | 2.8 | 3.3 | 3.4 |
| Plasma + FeCl3 (oxidized control) | 12.4 | 16.0 | 13.1 | 13.9 |
| 1.5 g DHA with 200 ml milk (microfluidized) | 44.0 | 42.6 | 45.8 | 44.1 |
| 1.75 g DHA, 1000 mg Vit E and 800 mg Vit C with 200 ml milk (not microfluidized) | 12.8 | 19.2 | 20.1 | 17.4 |
| 1.75 g DHA, 1000 mg Vit E and 800 mg Vit C with 200 ml milk (microfluidized) | 4.0 | 6.0 | 3.5 | 4.5 |
| 1.75 g DHA and 800 mg Vit C with 200 ml milk (microfluidized) | 17.5 | 17.8 | 20.8 | 18.7 |
| 1.75 g DHA and 1000 mg Vit E with 200 ml milk (microfluidized) | 9.8 | 16.7 | 11.4 | 12.6 |

The ROS load within any nanoemulsion preparation can be quantitatively determined by measuring indicators of an oxidizing environment. Malondialdehyde (MDA), is a known indicator of an oxidizing environment.

As can be seen in Table 1 above, the process of making a microfluidized nanoemulsion increases MDA levels by approximately 13-fold. Further, the presence of both vitamin C and/or vitamin E completely prevented MDA generation in microfluidized nanoemulsions thereby returning MDA to homeostatic plasma levels.

EXPERIMENTAL

The following examples are specific embodiments as contemplated by the present invention and are not intended to be limiting.

Example 1: Stable Formulation of Plant Sterol Microfluidized Nanoemulsions

This example presents one plant sterol embodiment of a microfluidized nanoemulsion. The step-wise procedure is as follows:

1. Heat 4 g of soybean oil
2. Add 5 g soy lecithin, stir and heat to 90° C.
3. Add 1 g plant sterol, stir and heat 10 mins
4. Add 250 mg polysorbate 80.
5. Heat 240 mL de-ionized water to 70° C.
6. Add step 4 mixture to step 5 mixture, keep stir bar and heat on for 30 mins
7. Homogenize step 6 mixture for 2-4 mins
8. Stir formulation for 10 mins on hot plate
9. Microfluidize using a M-1 10EH unit once at 25,000 PSI
10. Do particle diameter analysis using a Malvern Nano S instrument The mean particle diameter (i.e., Peak I/Peak 2) for these microfluidized plant sterol nanoemulsions was 39 nm. See FIG. 1A. The average particle diameter data for the plant sterol microfluidized nanoemulsion is shown in Table 2 below.

TABLE 2

Microfluidized Plant Sterol Nanoemulsion

| | Diam. (nm) | % Intensity | Width (nm) |
|---|---|---|---|
| Peak 1: | 54.16 | 85.86 | 14.36 |
| Peak 2: | 15.55 | 14.14 | 2.521 |
| Peak 3: | 0 | 0 | 0 |

Z-Average: 38.91;
PDI: 0.228;
Intercept: 0.9764.

Figure 1B:
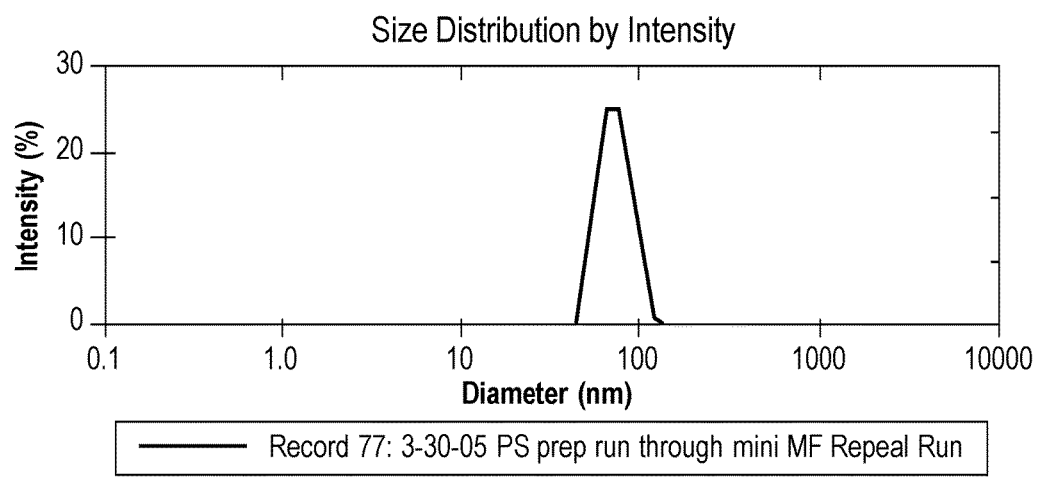
FIG. 1B presents exemplary data showing the particle diameter distribution of a microfluidized plant sterol nanoemulsion three (3) months after preparation.

After three months the particle diameter was again determined. The mean particle diameter (i.e., Peak 1) for this microfluidized plant sterol nanoemulsion was 64.4 nm. See FIG. 1 A. The average particle diameter data for the three month plant sterol nanoemulsion is shown in Table 3 below.

TABLE 3

Three Month Storage: Microfluidized Plant Sterol Nanoemulsion

| | Diam. (nm) | % Intensity | Width (nm) |
|---|---|---|---|
| Peak 1: | 74.8 | 100 | 120.8 |
| Peak 2: | 0 | 0 | 0 |
| Peak 3: | 0 | 0 | 0 |

Z-Average: 64.4; PDI: 0.196;
Intercept: 0.969.

Example 2: Stable Formulation of Cod Liver Oil Microfluidized Nanoemulsions

Figure 2:
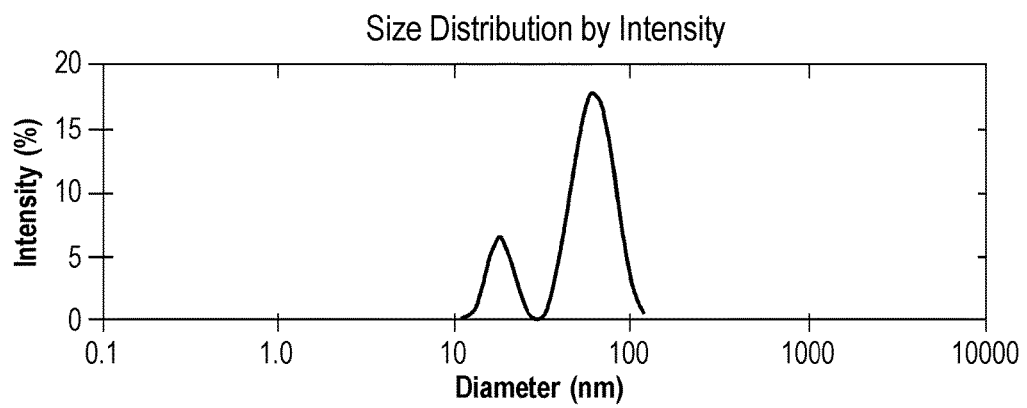
FIG. 2 presents exemplary data showing the particle diameter distribution of a microfluidized cod liver oil nanoemulsion population four (4) months after preparation.

This example presents one cod liver oil embodiment of a microfluidized nanoemulsion that has a stable particle diameter for at least four months. The step-wise procedure is as follows:

1. Heat 5 g of soybean oil (65° C.)
2. Add 5 g cod liver oil, stir and heat to 80° C.
3. Add 6 g polysorbate 80, stir and heat 20 mins
4. Add 200 mL de-ionized water, stir and heat 30 mins
5. Microfluidize using a M-1 10EH unit once at 25,000 PSI
6. Do particle diameter analysis using a Malvern Nano S instrument The mean particle diameter (i.e., Peak I/Peak 2) for this cod liver oil microfluidized nanoemulsion was 58 nm. Before microfluidization, the mean particle diameter of the cod liver oil suspension was 2,842 nm. This represents a 50-fold reduction with a single pass through the microfluidizer. Four months after the microfluidization process, the particle diameter was again determined and found not to have changed. See FIG. 2. The average particle diameter data from the four-month microfluidized sample is presented in Table 4.

TABLE 4

Microfluidized Cod Liver Oil Nanoemulsion Four Months After Preparation

|  | Diam. (nm) | % Intensity | Width(nm) |
|---|---|---|---|
| Peak 1: | 63.92 | 82.22 | 15.62 |
| Peak 2: | 18.51 | 17.78 | 2.771 |
| Peak 3: | 0 | 0 | 0 |

Z-Average: 45.15;
PDI: 0.247;
Intercept: 0.9707.

Example 3: Stable Formulation of Tocopherol Microfluidized Nanoemulsions

Figure 3:
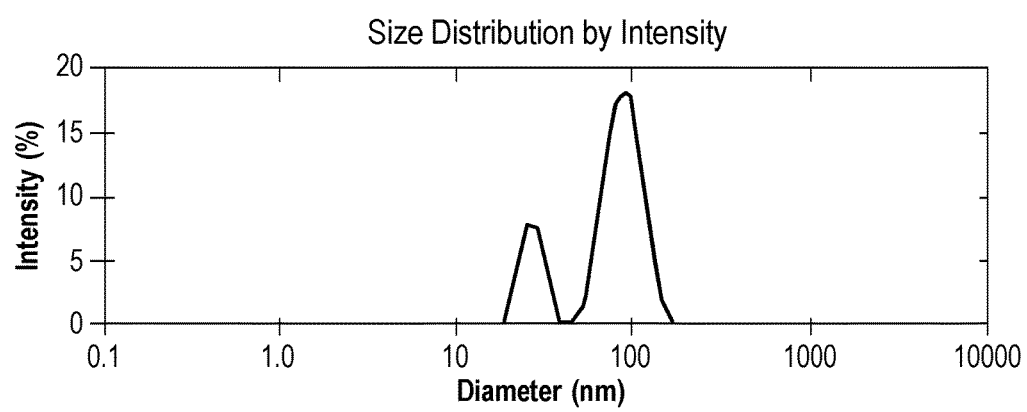
FIG. 3 presents exemplary data showing the particle diameter distribution of a microfluidized tocopherol nanoemulsion population five (5) months after preparation.

This example presents one tocopherol embodiment of a microfluidized nanoemulsion that maintains particle diameter for at least five months. The step-wise procedure is as follows:
1. Heat 13.5 g of soybean oil
2. Add 2 g tocopherol, stir and heat to 90° C.
3. Heat 2 g polysorbate 80 in 1 OO mL de-ionized water, heat to 75° C.
4. Add step 3 mixture to step 2 mixture
5. Heat 300 mL di-ionized water and 6 g polysorbate 80, heat till 70° C.
6. Add step 4 mixture to step 5 mixture, keep stir bar and heat on
7. Homogenize step 6 mixture for 2-4 mins
8. Stir formulation for 3-5 mins on hot plate
9. Microfluidize using a M-1 10EH unit once at 25,000 PSI
10. Do particle diameter analysis using a Malvern Nano S instrument The mean particle diameter for the tocopherol microfluidized nanoemulsion was 64 nm. Before microfluidization, the mean particle diameter for the tocopherol suspension was 1,362 nm. This represents a 21-fold reduction a single pass through the microfluidizer. Five months after the microfluidization process, the particle diameter was again determined and found not to have changed. See FIG. 3. The average particle diameter data from the five-month microfluidized sample is presented in Table 5.

TABLE 5

Microfluidized Tocopherol Nanoemulsion Five Months After Preparation

|  | Diam. (nm) | % Intensity | Width (nm) |
|---|---|---|---|
| Peak 1 | 88.06 | 77.84 | 19.99 |
| Peak 2 | 26.46 | 22.16 | 3.651 |
| Peak 3 | 0 | 0 | 0 |

Z-Average: 58.07;
PDI: 0.234;
Intercept 0.9697

Figure 4:
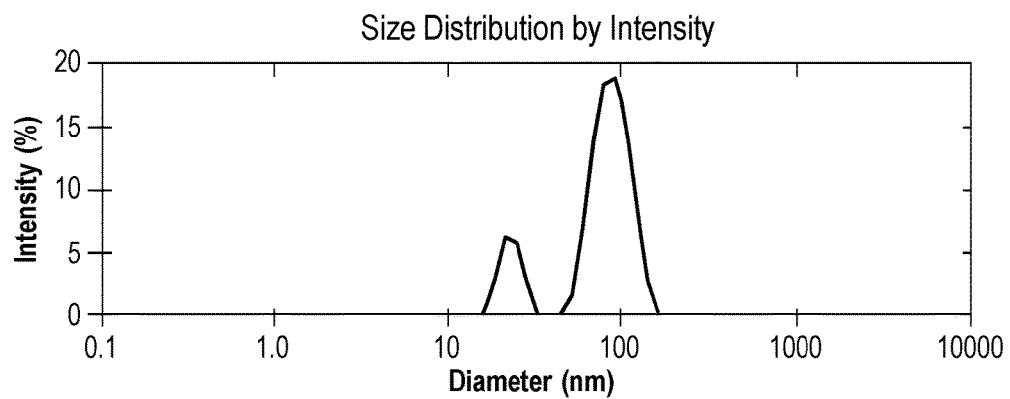
FIG. 4 presents exemplary data showing the particle diameter distribution of a microfluidized lutein/zeaxanthin nanoemulsion population.

Example 4: Formulation of Lutein and Zeaxanthin Microfluidized Nanoemulsions This example presents one lutein/zeaxanthin embodiment of a microfluidized nanoemulsion. The step-wise procedure is as follows:
1. Heat 5 g of soybean oil
2. Add 2 g of lecithin
3. Heat and stir, 10 mins
4. Add 125 mg of lutein and 125 mg of zeaxanthin
5. Heat and stir, 10 mins
6. Heat 240 ml de-ionized water, 50° C.
7. Add heated water to mixture
8. Stir and heat, till it is a solution
9. Microfluidize using a M-1 10EH unit once at 25,000 PSI
10. Do particle diameter analysis using a Malvern Nano S instrument The mean particle diameter (i.e., Peak I/Peak 2) for the lutein and zeaxanthin microfluidized nanoemulsion was 62 nm. See FIG. 4. The average particle diameter data for the sample is shown in Table 6.

TABLE 6

Microfluidized Lutein/Zeaxanthin Nanoemulsion

|  | Diam. (nm) | % Intensity | Width (nm) |
|---|---|---|---|
| Peak 1 | 89.45 | 83.96 | 21.1 |
| Peak 2 | 22.81 | 16.04 | 2.968 |
| Peak 3 | 0 | 0 | 0 |

Z-Average: 62.26
PDI: 0.245
Intercept: 0.976

Example 5: Formulation of Soy Protein Microfluidized Nanoemulsion

Figure 5:
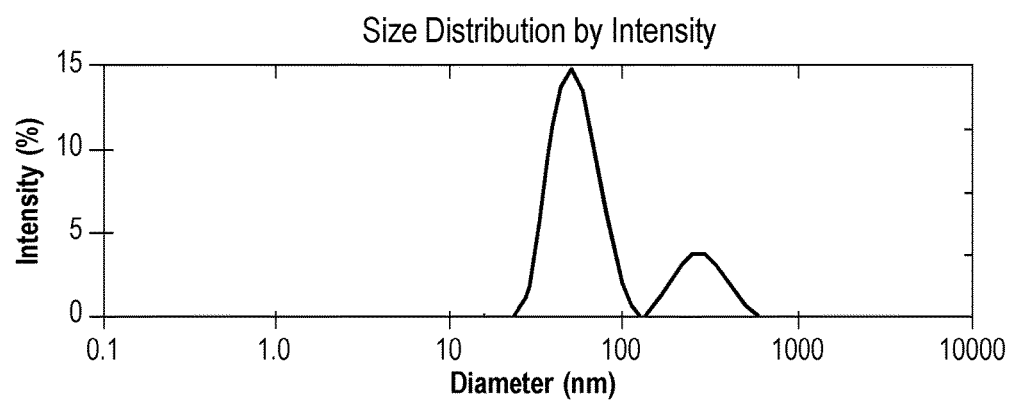
FIG. 5 presents exemplary data showing the particle diameter distribution of a microfluidized soy protein nanoemulsion population.

This example presents one soy protein embodiment of a microfluidized nanoemulsion. The step-wise procedure is as follows:
1. Heat 5 g soybean oil
2. Add 5 g liquid lecithin
3. Heat and stir 10 mins, 70° C.
4. Heat 240 mL de-ionized water, 65° C.
5. Add heated water to mixture
6. Add 9 g soy protein, stir and heat 10 min
7. Add 9 g soy protein
8. Stir and heat 20 min, 70° C.
9. Homogenize 1 min
10. Microfluidize using a M-110EH unit ten times at 25,000 PSI
11. Do particle diameter analysis using a Malvern Nano S instrument The mean particle diameter (i.e., Peak I/Peak 2) for the vanilla soy protein (Central Soya) microfluidized nanoemulsion was 55 nm. See FIG. 5. The average particle diameter data for the sample is shown in Table 7.

TABLE 7

Microfluidized Soy Protein Nanoemulsion

|  | Diam. (nm) | % Intensity | Width (nm) |
|---|---|---|---|
| Peak 1 | 55.15 | 80.32 | 16.45 |
| Peak 2 | 290.8 | 19.68 | 82.82 |
| Peak 3 | 0 | 0 | 0 |

Z-Average: 54.97;
PDI: 0.283;
Intercept: 0.9819

Example 6: Formulation of Whey Protein Microfluidized Nanoemulsion

Figure 6:
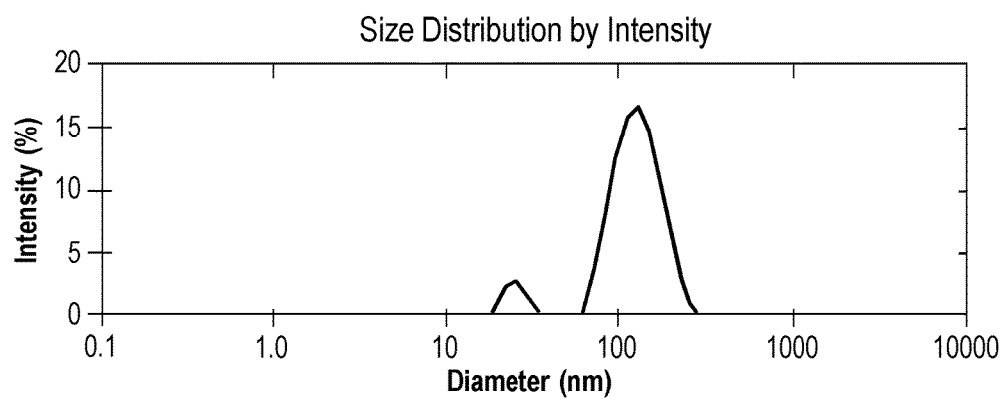
FIG. 6 presents exemplary data showing the particle diameter distribution of a microfluidized whey protein nanoemulsion population.

This example presents one whey protein embodiment of a microfluidized nanoemulsion. The step-wise procedure is as follows:

1. Heat 5 g soybean oil
2. Add 5 g soy lecithin
3. Add 250 mg polysorbate 80
4. Heat and stir 10 mins, 70° C.
5. Heat 240 mL de-ionized water, 65° C.
6. Add heated water to mixture
7. Add 10 g whey protein
8. Stir and heat 10 min
9. Homogenize 1 min
10. Microfluidize using a M-110EH unit once at 25,000 PSI
11. Do particle diameter analysis Malvern Nano S instrument The mean particle diameter (i.e., Peak I/Peak 2) for the whey protein microfluidized nanoemulsion was 108 nm. See FIG. 6. The average particle diameter data for the sample is shown in Table 8.

TABLE 8

Microfluidized Whey Protein Nanoemulsion

|        | Diam. (nm) | % Intensity | Width (nm) |
|--------|------------|-------------|------------|
| Peak 1 | 127.7      | 91.3        | 38.09      |
| Peak 2 | 23.72      | 6.161       | 2.764      |
| Peak 3 | 5027       | 2.536       | 593        |

Z-Average: 108.2
PDI: 0.263
Intercept: 0.948

Figure 7:
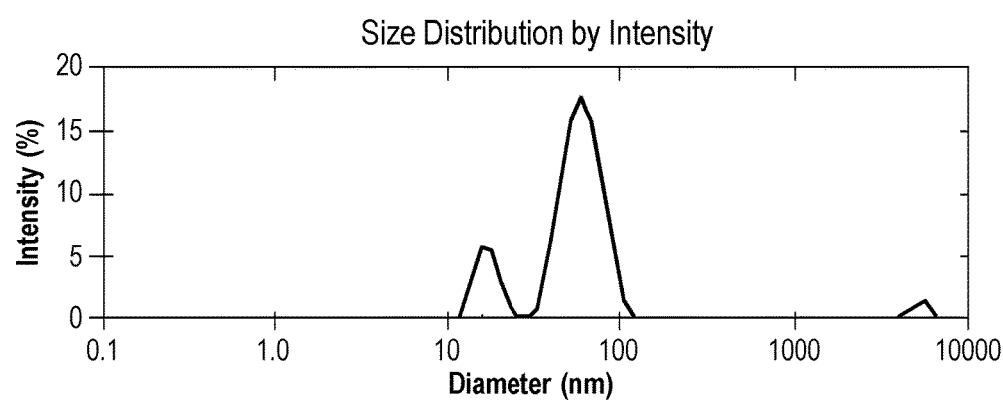
FIG. 7 presents exemplary data showing the particle diameter distribution of a microfluidized orange juice/plant sterol/lutein nanoemulsion population.

Example 7: Formulation of Orange Juice, Plant Sterol and Lutein Microfluidized Nanoemulsion This example presents one orange juice/plant sterol/lutein embodiment of a microfluidized nanoemulsion. The step-wise procedure is as follows:

1. Heat soybean oil, 80° C.
2. Add 1.5 g plant sterol
3. Stir and heat, 5 min
4. Add 5 g polysorbate 80
5. Add 70 mg Lutein
6. Stir and heat, 10 min
7. Add 240 mL orange juice (Tropicana®)
8. Stir and heat, 1 hour
9. Microfluidize using a M-110EH unit twice at 25,000 PSI
10. Do particle diameter analysis using a Malvern Nano S instrument The mean particle diameter (i.e., peak 1/Peak 2) for the orange juice/plant sterol/lutein microfluidized nanoemulsion was 46 nm. See FIG. 7. The average particle diameter data for the sample is shown in Table 9.

TABLE 9

Microfluidized Orange Juice/Plant Sterol/Lutein Nanoemulsion

|        | Diam. (nm) | % Intensity | Width (nm) |
|--------|------------|-------------|------------|
| Peak 1 | 61.55      | 81.57       | 15.32      |
| Peak 2 | 17.13      | 16.1        | 2.433      |
| Peak 3 | 5143       | 2.329       | 509.4      |

Z-Average: 46.41;
PDI: 0.322;
Intercept: 0.9609

Example 8: Stable Formulation of DHA Fish Oil/Water Microfluidized Nanoemulsion

Figure 8:
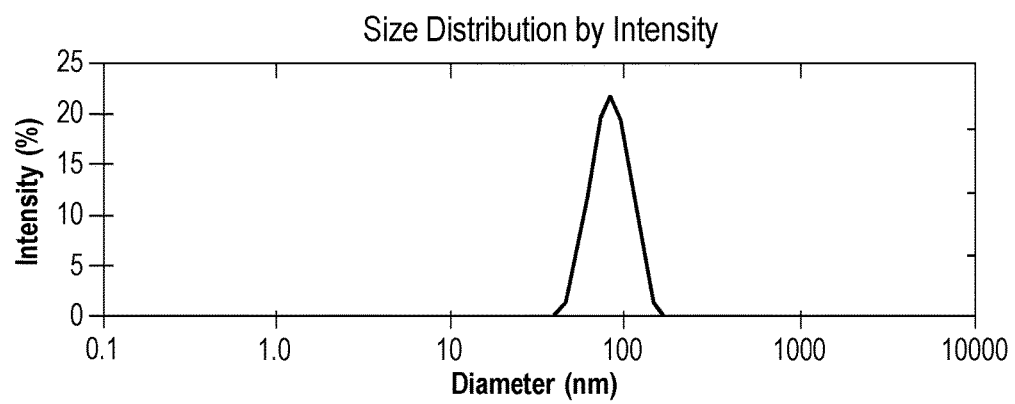
FIG. 8 presents exemplary data showing the particle diameter distribution of a microfluidized DHA fish oil/water nanoemulsion population two (2) months after preparation.

This example presents one DHA fish oil/water embodiment of a microfluidized nanoemulsions that maintains particle diameter for at least two months. The step-wise procedure is as follows:

1. Heat 6.4 g DHA fish oil
2. Add 6 g soy lecithin
3. Add 250 mg polysorbate 80
4. Heat 240 mL de-ionized water, 75° C.
5. Add heated water to mixture
6. Stir and heat, 20 mins
7. Homogenize 2 mins
8. Stir and heat, 10 mins
9. Microfluidize using a M-110EH unit once at 25,000 PSI
10. Do particle diameter analysis using a Malvern Nano S instrument The mean particle diameter (i.e., Peak 1) for the DHA fish oil/water microfluidized nanoemulsion was 73 nm. Two month s after the microfluidization process, the particle diameter was again determined and found not to have changed. See FIG. 8. The average particle diameter from the two-month microfluidized sample is presented in Table 10.

TABLE 10

Stable Microfluidized DHA Fish Oil/Water Nanoemulsion

|        | Diam. (nm) | % Intensity | Width (nm) |
|--------|------------|-------------|------------|
| Peak 1 | 81.73      | 100         | 20.38      |
| Peak 2 | 0          | 0           | 0          |
| Peak 3 | 0          | 0           | 0          |

Z-Average: 72.58;
PDI: 0.205;
Intercept: 0.9636.

Example 9: Stable Formulation of DHA Fish Oil/Milk Microfluidized Nanoemulsion

Figure 9:
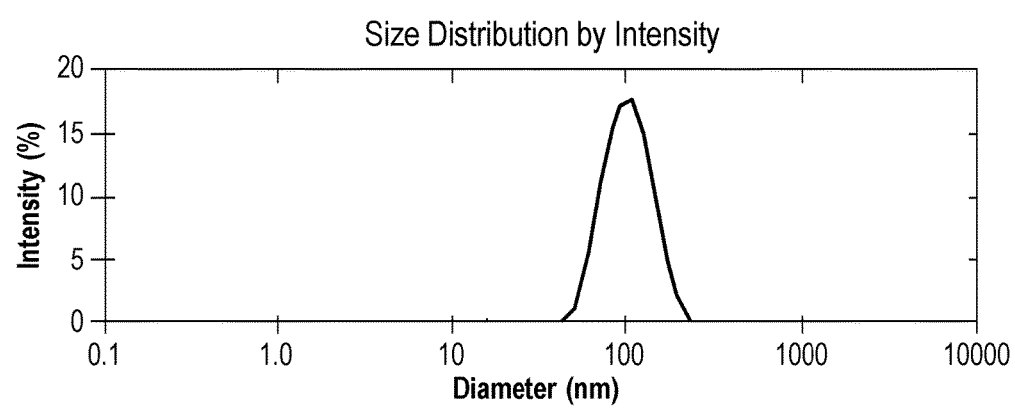
FIG. 9 presents exemplary data showing the particle diameter distribution of a microfluidized DHA fish oil/milk nanoemulsion population three (3) weeks after preparation.

This example presents one DNA fish oil/milk embodiment without any added emulsifiers that maintains particle diameter for at least three (3) weeks. The step-wise procedure is as follows:

1. Heat 1.5 g DHA fish oil, 50° C.
2. Heat 200 mL whole milk, 50° C.
3. Mix the two together
4. Stir and heat, 10 mins
5. Microfluidize using a M-1 10EH unit once at 25,000 PSI
6. Do particle diameter analysis using a Malvern Nano S instrument The mean particle diameter (i.e., Peak 1) for the DHA fish oil/milk microfluidized nanoemulsion 93 nm. This nanoemulsion preparation was made without any added emulsifiers. Three weeks after the microfluidization process, the fish oil was still in solution and the particle diameter was again determined and found not to have changed. See FIG. 9. The average particle diameter data from the three-week microfluidized sample is presented in Table 11.

TABLE 11

Stable Microfluidized DNA Fish Oil/Milk Nanoemulsion

|  | Diam. (nm) | % Intensity | Width (nm) |
|---|---|---|---|
| Peak 1 | 106.9 | 100 | 32.84 |
| Peak 2 | 0 | 0 | 0 |
| Peak 3 | 0 | 0 | 0 |

Z-Average: 93.11;
PDI: 0.178;
Intercept: 0.9341

Example 10: Temperature Stability of Microfluidized Nanoemulsions

Figure 10:
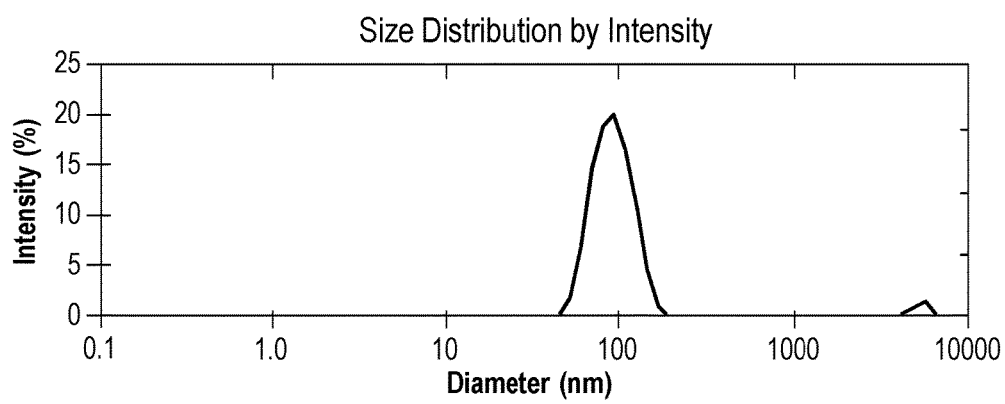
FIG. 10 presents exemplary data showing the particle diameter distribution of a microfluidized DHA fish oil/milk/ tocopherol nanoemulsion population.

This example presents the stability of microfluidized nanoemulsions following exposure to either heat or cold. The formulation used in this experiment comprised DHA Fish Oil milk/tocopherol.
1. Dissolved 1 g of vitamin C in 25 mL of di-ionized water
2. Added 200 mL of whole milk to step 1
3. Took 1.7 g DHA fish oil and added 800 mg of delta tocopherol
4. Added steps 1 and 2 to step 3
5. Stir and heat 10 mins, 50° C.
6. Microfluidize using a M-110EH unit once at 25,000 PSI
7. Do particle diameter analysis using a Malvern Nano S instrument The mean particle diameter (i.e., Peak 1) for the DHA fish oil/milk/tocopherol microfluidized nanoemulsion was 87 nm. See FIG. 10. This nano-emulsion preparation was made without any added emulsifiers. The average particle diameter data for the original nanoemulsion is presented in Table 12.

TABLE 12

Microfluidized DNA Fish Oil/Milk/Tocopherol Original Nanoemulsion

|  | Diam. (nm) | % Intensity | Width (nm) |
|---|---|---|---|
| Peak 1 | 91.84 | 97.86 | 23.95 |
| Peak 2 | 5179 | 2.144 | 485.1 |
| Peak 3 | 0 | 0 | 0 |

Z-average: 87.09;
PDI: 0.216;
Intercept: 0.9339

Figure 11:
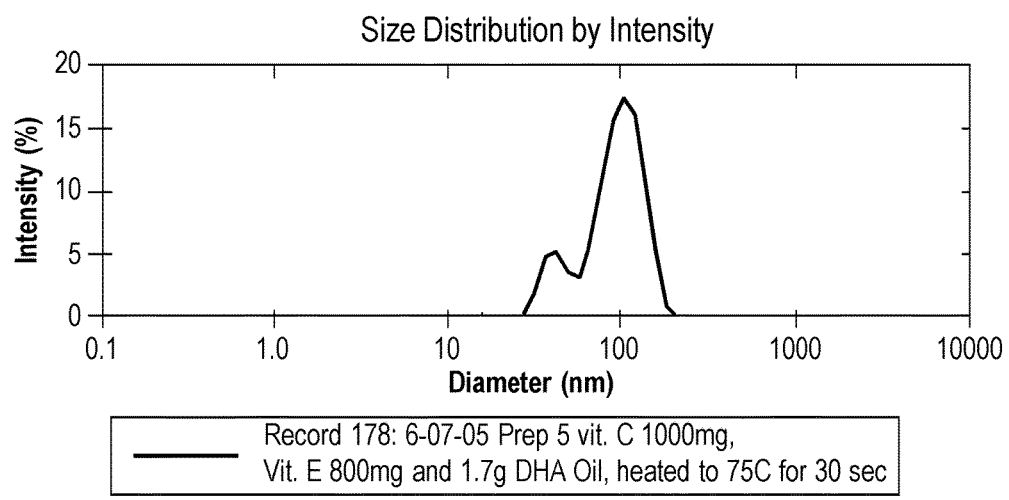
FIG. 11 presents exemplary data showing the particle diameter distribution of a microfluidized DHA fish oil/milk/ tocopherol nanoemulsion population after pasteurization.

This original microfluidized nanoemulsion was pasteurized at 75° C. for 30 seconds. Twenty-four hours later, the oil was still in solution and the particle diameter was stable as compared to the original nanoemulsion. See FIG. 11. The average particle diameter data for the pasteurized microfluidized nanoemulsion is presented in Table 13.

TABLE 13

Microfluidized DHA Fish Oil/Milk/Tocopherol Pasteurized Nanoemulsion

|  | Diam. (nm) | % Intensity | Width (nm) |
|---|---|---|---|
| Peak 1 | 108.3 | 82.49 | 28.06 |
| Peak 2 | 45.16 | 17.51 | 8.109 |
| Peak 3 | 0 | 0 | 0 |

Z-Average: 87.18;
PDI: 0.198;
Intercept: 0.9281

Figure 12:
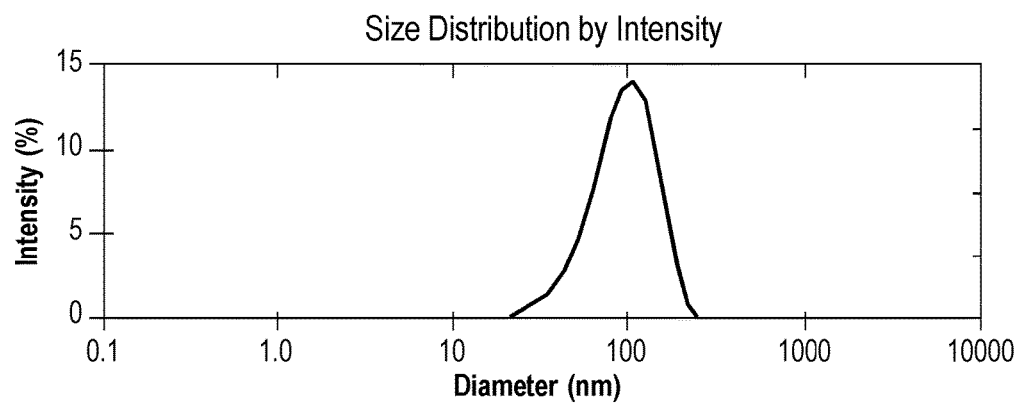
FIG. 12 presents exemplary data showing the particle diameter distribution of a microfluidized DHA fish oil/milk/ tocopherol nanoemulsion population after a freeze-thaw process.

The original microfluidized nanoemulsion was freeze-thaw tested at −4° C. for 24 hours. Twenty-four hours later, the oil was still in solution and the particle diameter was stable as compared to the original nanoemulsion. See FIG. 12. The average particle diameter data for the freeze-thaw microfluidized nanoemulsion is presented in Table 14.

TABLE 14

Microfluidized DHA Fish Oil/Milk/Tocopherol Freeze-Thaw Nanoemulsion

|  | Diam. (nm) | % Intensity | Width (nm) |
|---|---|---|---|
| Peak 1 | 99.72 | 100 | 39.07 |
| Peak 2 | 0 | 0 | 0 |

Z-Average: 87.58;
PDI: 0.198

Example 11: Improved Bioavailability of Dietary Lycopene

This example demonstrates an improved bioavailability of lycopene when fed as a uniform microfluidized nanoemulsion versus mixed into a standard diet formulation.

The lycopene microfluidized nanoemulsion was prepared in a step-wise manner as follows:
1. Heat 5 g of soybean oil
2. Add 2 g of lecithin
3. Heat and stir, 10 mins
4. Add 125 mg of lycopene
5. Heat and stir, 10 mins
6. Heat 240 ml de-ionized water (or grape juice); 50° C.
7. Add heated water (or grape juice) to mixture
8. Stir and heat, till it is a solution
9. Microfluidize using a M-110EH unit once at 25,000 PSI
10. Do particle diameter analysis using a Malvern nano S instrument The mean particle diameter for the lycopene microfluidized nanoemulsion was 74 nm.

Bioavailability in Gerbils

The microfluidized nanoemulsion was incorporated into a chow-based diet and fed to gerbils over a 4 week period. A control group was fed a lycopene in oil-enriched chow-based diet. At the end of 4 weeks, blood was collected, plasma harvested and plasma lycopene levels were determined by HPLC in both gerbil groups.

Figure 13:
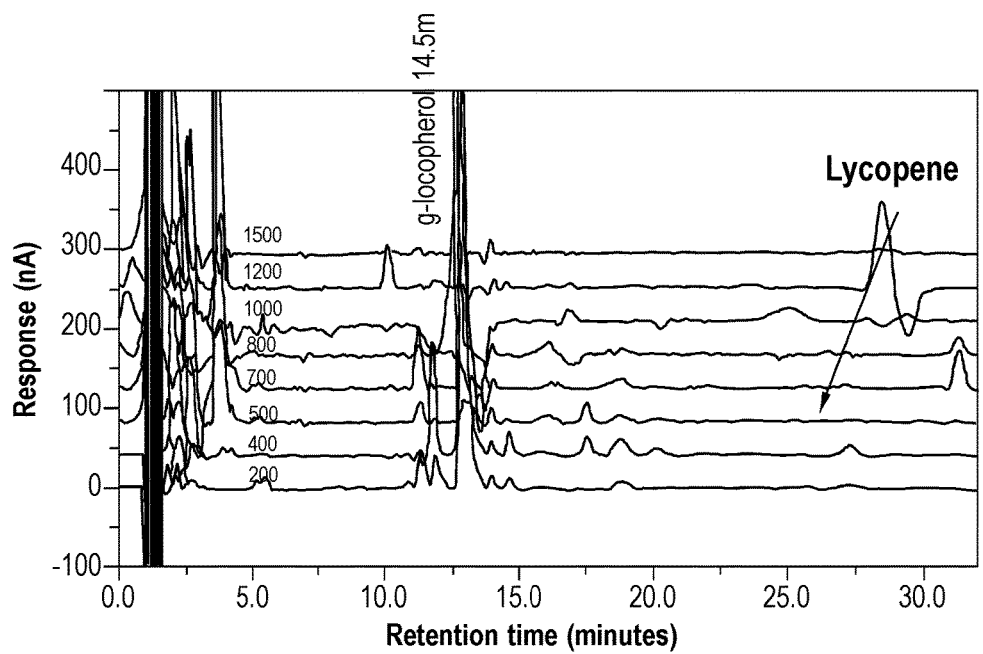
FIG. 13 presents exemplary data of gerbil plasma lycopene levels when fed a lycopene-enriched diet.
Figure 14:
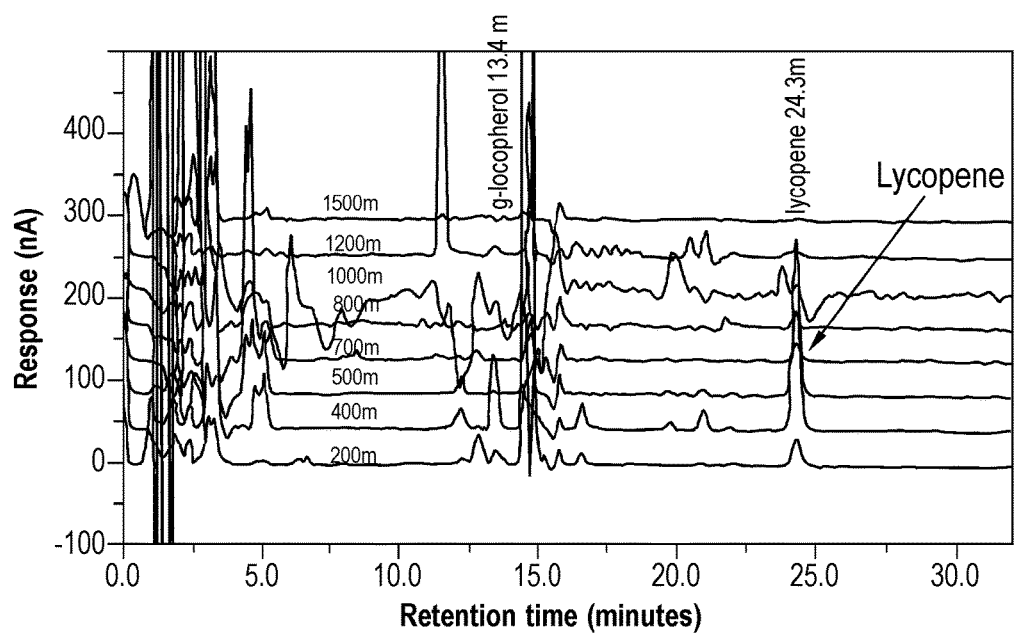
FIG. 14 presents exemplary data of gerbil plasma lycopene levels when fed a microfluidized lycopene nanoemulsion diet

FIG. 13 demonstrates that control gerbils did not demonstrate detectable plasma lycopene levels. The gerbils fed a chow comprising a microfluidized lycopene nanoemulsion, however, demonstrated elevated plasma lycopene levels. See FIG. 14.

Bioavailability in Humans

A microfluidized lycopene nanoemulsion was then prepared with grape juice instead of water and orally administered to two (2) human subjects over a 4 day period (125 mg/serving, 2 servings per day). This administration raised plasma lycopene levels by approximately 38% (data not shown).

Example 12: Improved Efficacy of Microfluidized Nanoemulsions

This example presenting data showing that microfluidized nanoemulsions provide improved efficacy over that seen in traditional nanoemulsions. Specifically, this example compares the ability of three plant sterol formulations to reduce plasma low density lipoprotein cholesterol (LDL-C) levels in hypercholesterolemic hamsters.

A microfluidized mixed plant sterol (60% sitosterol) nanoemulsion was prepared in a step-wise manner as follows:

1. Heat 5 g soybean oil.
2. Add 5 g soy lecithin, stir and heat 15 mins.
3. Repeat Step 2.
4. Add 15 g soybean oil, stir and heat 10 mins.
5. Add 4 g plant sterol, stir and heat 10 mins.
6. Repeat Step 4 four (4) times.
7. Add 1 g polysorbate 80, stir and heat 10 mins.
8. Heat 200 ml MinuteMaid Heartwise® orange juice (75° C.).
10. Heat 1800 ml MinuteMaid Heartwise® orange juice (70° C.).
11. Add Step 8 to Step 7. Stir and heat 20 min (80° C.).
12. Add to Step 10.
13. Add 1 g polysorbate 80, stir and heat 20 min (80° C.).
14. Homogenize for 2-4 min.
15. Stir homogenate on hot plate for 10 min.
16. Microfluidize using a M-1 10EH unit at 25,000 PSI.
17. Do particle analysis using a Malvern Nano S instrument.

Figure 16:
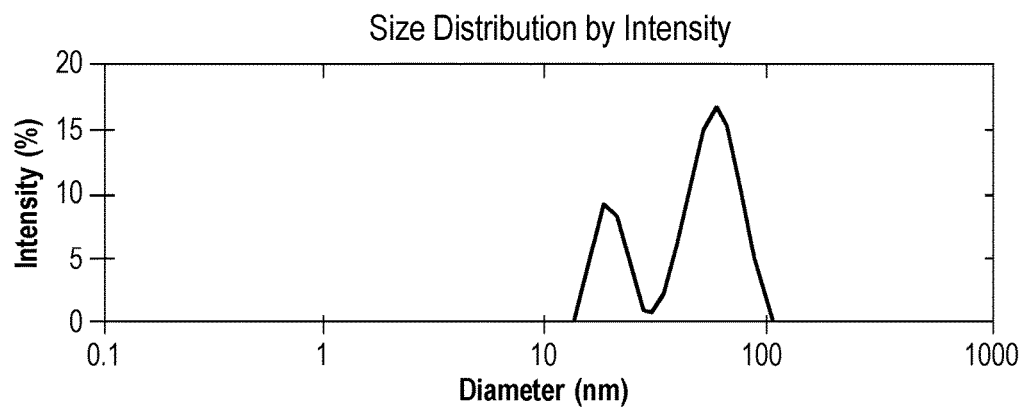
FIG. 16 presents exemplary data showing the particle diameter distribution of a microfluidized plant sterol nanoemulsion population used in Example 12.

The mean particle diameter for the microfluidized plant sterol nanoemuision was 41.95 nm. See FIG. 16.

Figure 17:
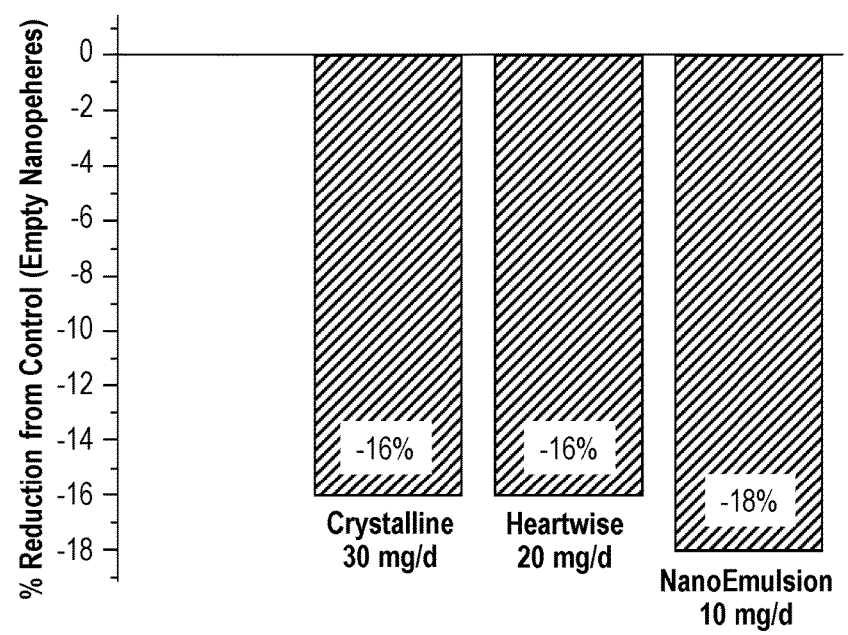
FIG. 17 presents exemplary data showing that a microfluidized plant sterol nanoemulsion diet is more effective in reducing plasma LDL-C in hypercholesterolemic hamsters than either a micronized plant sterol diet or a crystalline plant sterol diet for four (4) weeks.

Forty (40) hamsters were divided into four (4) groups often (10) each. Group 1 was fed a control hypercholesterolemic diet (HCD); Group 2 was fed 30 mg/d of crystalline plant sterol; Group 3 was fed 20 mg/d of MinuteMaid Heartwise® micronized plant sterol (Cargill); Group 4 was fed 10 mg/d of the microfluidized plant sterol nanoemuision. After four (4) weeks, blood samples were analyzed for plasma LDL-C levels. The microfluidized plant sterol nanoemulsion was twice as effective as the MinuteMaid Heartwise® micronized diet, and three times as effective as the crystalline plant sterol diet. See FIG. 17.

The data show that the improved bioavailability shown in Example 11 results in improved clinical therapy when compared to micron-sized or crystalline plant sterol diets.

Example 13: Cholesterol Nanoemulsions: Insoluble Vs Soluble Dispersion Media

This example presents data demonstrating that uniform microfluidized nanoemulsion compositions depend upon a compound having substantial solubility in the liquid dispersion medium. This example compares the microfluidizing technique described in U.S. Pat. No. 5,510,118 to one embodiment as contemplated by the present invention. The absorbable lipid cholesterol was chosen as the test compound.

Figure 18A:
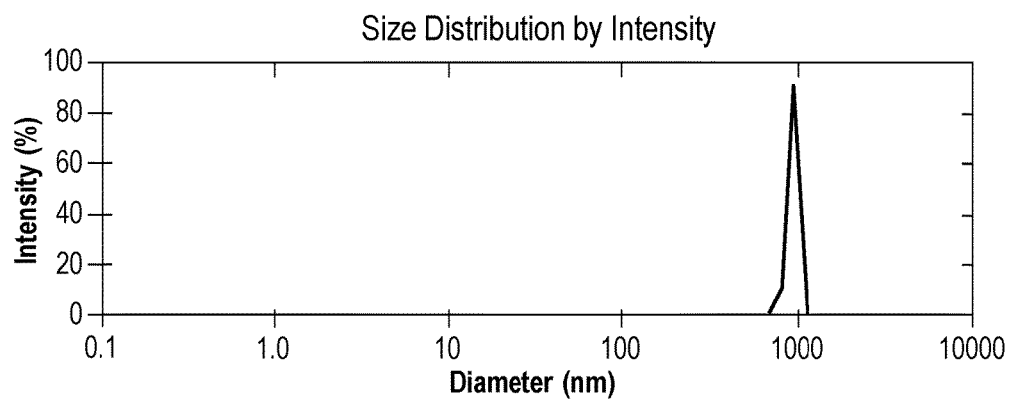
Figure 18B:
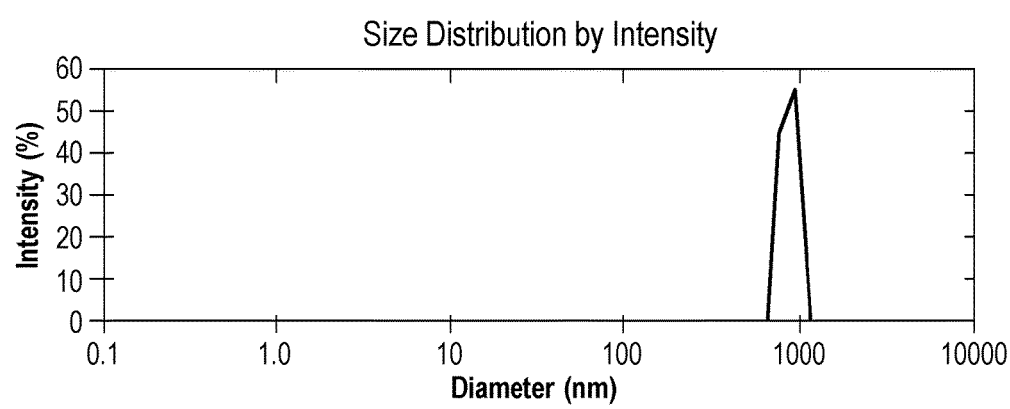

Group I represents the '118 premix and was prepared by dispersing cholesterol (2 gms), water (100 mls) and Tween® 80 (0.2 gms), where cholesterol is insoluble (i.e., below at least 30 mg/ml) in the liquid dispersion medium (water). Thereafter, this cholesterol/water/Tween® 80 solution was microfluidized using a M-100EH unit. Multiple passes (10-15) through the microfluidizer were performed at PSI's ranging between 4,000-20,000 but were terminated because the generated heat exceeded 70° C. (much higher than the recommended 30-40° C. in the '118 patent. After the microfluidization it was observed that much of the cholesterol had precipitated. After twenty-four hours, the preparation of the Group I nanoemulsion contained only 0.44 gms (i.e., 22%) of the original cholesterol weight Group II represents one embodiment of the present invention and was prepared by dispersing cholesterol (2 gms) in heated soybean oil (10 gms), soy lecithin (5 gms), and Tween® 80 (0.2 gms) where cholesterol is substantially soluble (i.e., above at least 30 mg/ml) in the dispersion medium (oil). Thereafter, this cholesterol/oil/lecithin/Tween® 80 was added to 100 ml of heated water and microfluidized using a single 30 second pass at 25,000 PSI using a M-100EH unit. After the microfluidization cholesterol precipitation was not noticeably evident. After twenty-four hours, the preparation of the Group II nanoemulsion contained 1.66 gm (i.e., 83%) of the original cholesterol weight The data show that the particle diameter distributions from both Group I and Group II premix preparations are practically identical. See FIG. 18A and FIG. 18B, respectively. Specifically, a single peak ranging from 700-1000 nm having a mean particle diameter of approximately 900 nm is observed for both preparations. See Tables 15 and 16.

TABLE 15

Cholesterol/Tween ® 80/Water Premix Particle diameter: Group I

| | Diam. (nm) | % Intensity | Width (nm) |
| --- | --- | --- | --- |
| Peak 1 | 942.5 | 100 | 38.9 |

Z-Average: 1982;
PDI: 0.210;
Intercept: 0.6797

TABLE 16

Cholesterol/Oil/Lecithin/Tween ® 80/Water Premix Particle diameter: Group II

| | Diam. (nm) | % Intensity | Width (nm) |
| --- | --- | --- | --- |
| Peak 1 | 897.9 | 100 | 64.8 |

Z-Average: 1328;
PDI: 0.427;
Intercept: 0.6989

Figure 19A:
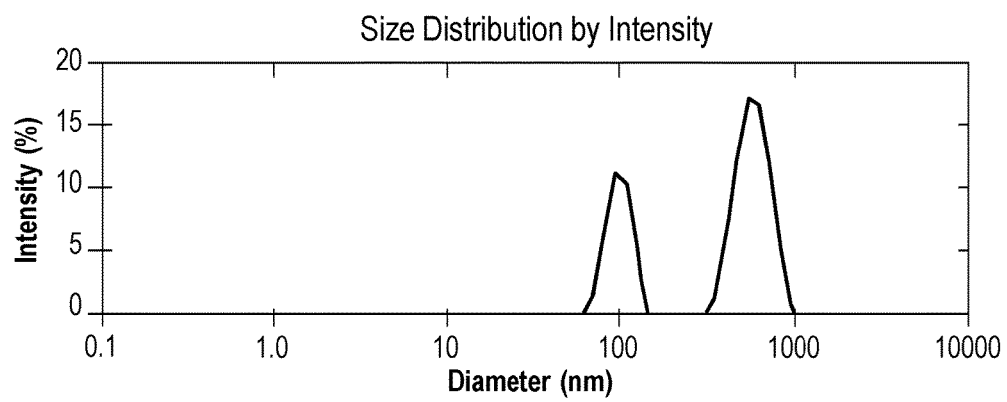
Figure 19B:
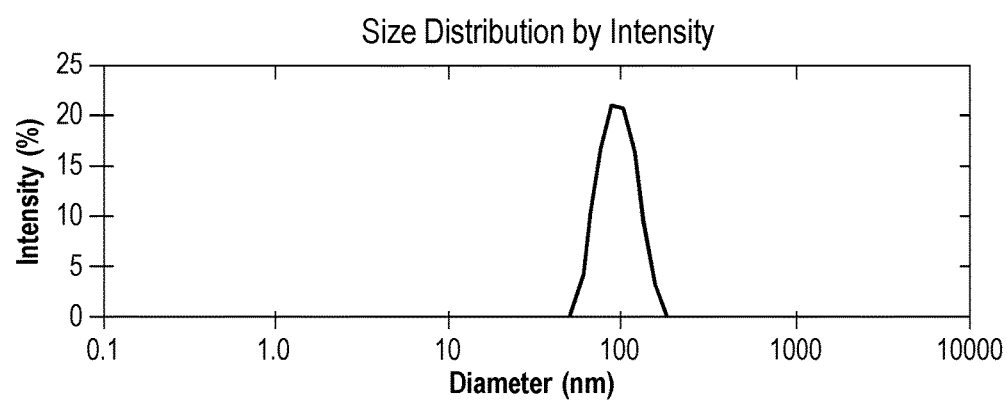

Following microfluidization, however, the particle diameter distributions are vastly different between Group 1 and Group II. See FIG. 19A and FIG. 19B, respectively. Group I shows two vastly disparate and distinct peaks. See Table 17. Group II, however, shows a single peak representing one embodiment of a uniform microfluidized nanoemulsion. See Table 18.

TABLE 17

Microfluidized Cholesterol/Tween ® 80/Water Nanoemulsion

| | Diam. (nm) | % Intensity | Width (nm) |
| --- | --- | --- | --- |
| Peak 1 | 578.2 | 67.6 | 120.8 |
| Peak 2 | 96.7 | 32.3 | 14.9 |

Z-Average: 246.5;
PDI: 0.789;
Intercept: 0.7687

TABLE 18

Microfluidized Cholesterol/Oil/Lecithin/
Tween ® 80/Water Nanoemulsion

|  | Diam. (nm) | % Intensity | Width (nm) |
|---|---|---|---|
| Peak 1 | 101.3 | 100 | 25.1 |

Z-Average: 86.8;
PDI: 0.240;
Intercept: 0.9455

The data above demonstrate that some embodiments of the present invention contemplate improvements over the art in creating uniform microfluidized nanoemulsions. In particular, it is now clear that the Bosch et al ('118 patent), and the Cooper et al. portfolio ('758, '038, and '202 application publications) do not teach a microfluidization process that creates a uniform particle diameter distribution.

Example 14: Nanoparticulate Compositions vs Uniform Microfluidized Nanoemulsions This example describes a demonstration that will show that a milled nanoparticle composition (for example, one made according to USAppln PublNo. 2004/0033202 to Cooper et al.) does not create a uniform particle diameter distribution as does a microfluidized nanoemulsion as contemplated by one embodiment of the present invention. An absorbable phytosterol will be chosen as the test compound.

Group I represents the '202 premix that will be prepared by dispersing 5% (w/w) phytosterol/water solution with 1% (w/w) Tween® 80, where the phytocholesterol is insoluble (i.e., below at least 30 mg/ml) in the liquid dispersion medium (water). Thereafter, this phytosterol/water/Tween® 80 solution will be milled at 10° C. for 1.5 to 2 hours in a DYNO®-Mill KDL (Willy A Bachofen AG, Machinefabrik, Basel, Switzerland) using a 500 \xm milling media (i.e., grinding beads) of type Polymill® 500. After the milling it will be observed that much of the phytocholesterol has precipitated. After at least twenty-four hours, the preparation of the Group I nanoparticulate will contain less than 1⁄4 of the original phytosterol weight.

Group II represents one embodiment of the present invention and will be prepared by dispersing 5% (w/w) phytosterol/heated soybean oil solution, soy lecithin, with 1% Tween® 80, where the phytosterol is substantially soluble (i.e., above at least 30 mg/ml) in the liquid dispersion medium (oil). Thereafter, this phytosterol/oil/lecithin/Tween® 80 premix is added to 100 ml heated water and microfluidized using a single 30 second pass at 25,000 PSI using a M-100EH unit. After the microfluidization phytosterol precipitation will not be noticeably evident. After twenty-four hours, the preparation of the Group II nanoemulsion will contain greater than 3⁄4 of the original phytosterol weight.

The data will show that the particle diameter distributions from both Group I and Group II premix preparations are practically identical. For example, a single peak ranging from 700-1000 nm having a mean particle diameter of approximately 900 nm might be observed for both preparations. See Tables 19 and 20.

TABLE 19

Phytosterol/Tween 80/Water Premix Particle diameter: Group I

|  | Diam. (nm) | % Intensity | Width (nm) |
|---|---|---|---|
| Peak 1 | 942.5 | 100 | 38.9 |

Z-Average: 1982;
PDI: 0.210;
Intercept: 0.6797

TABLE 20

Phytosterol/Oil/Lecithin/Tween 80/Water
Premix Particle diameter: Group II

|  | Diam. (nm) | % Intensity | Width (nm) |
|---|---|---|---|
| Peak 1 | 897.9 | 100 | 64.8 |

Z-Average: 1328;
PDI: 0.427;
Intercept: 0.6989

Following processing however, the particle diameter distributions are expected to be vastly different between Group I and Group II. For example, Group I will most likely show at least two vastly disparate and distinct peaks. See Table 21. Group II, however, will have only a single peak representing one embodiment of a uniform microfluidized nanoemulsion. See Table 22.

TABLE 21

Microfluidized Cholesterol/Tween 80/Water Nanoemulsion: Group I

|  | Diam. (nm) | % Intensity | Width (nm) |
|---|---|---|---|
| Peak 1 | 578.2 | 67.6 | 120.8 |
| Peak 2 | 96.7 | 32.3 | 14.9 |

Z-Average: 246.5;
PDI: 0.789;
Intercept: 0.7687

TABLE 22

Microfluidized Cholesterol/Oil/Lecithin/Tween
80/Water Nanoemulsion: Group II

|  | Diam. (nm) | % Intensity | Width (nm) |
|---|---|---|---|
| Peak 1 | 101.3 | 100 | 25.1 |

Z-Average: 86.8;
PDI: 0.240;
Intercept: 0.9455

The data above demonstrate that nanoparticulate composition are not able to create uniform particle diameter distributions as contemplated by some embodiments of the nanoemulsions contemplated herein. In particular, it is now clear that the Cooper et al. portfolio ('758, '038, and '202 application publications) do not teach a milling process that creates a uniform particle diameter distribution.

Example 15: Improved Bioavailability Over Conventional Nanoparticulate Compositions This example will provide data showing that a uniform microfluidized nanoemulsion as contemplated by one embodiment of the present invention has improved plant sterol bioavailability and/or efficacy than a conventional nanoparticulate composition.

A standard curve will be constructed by gavaging thirty (30) hamsters with 1 µCi $^3$H-cholesterol. Plasma cholesterol levels are then determined at Day 1, Day 2, Day 4, and Day 7. These data are used to calculate bioavailability of $^3$H-cholesterol during the 7 Day period as area-under-the-curve (AUC).

After plasma radioactivity levels have returned to background levels (i.e., approximately 7.5 cholesterol metabolic half-lives), the experiment will be repeated using the following treatment groups (n=10).

Group I: Standard diet mixed with a plant sterol.
Group II: Standard diet mixed with a uniform microfluidized plant sterol nanoemulsion prepared in accordance with Example 1,
Group III: Standard diet mixed with a conventional lycopene nanoparticulate composition prepared in accordance with conventional milling grinder techniques as described in the '202 Cooper et al. application.

The AUC measurement will determine the ability of each preparation to reduce the absorption of $^3$H-cholesterol into the bloodstream which is proportional to the bioavailability and/or efficacy of each preparation, A greater bioavailability and/or efficacy of a plant sterol when administered as a uniform microfluidized nanoemulsion will be seen because: i) the average particle diameter of the uniform microfluidized nanoemulsion is smaller than the conventional nanoparticulate composition (i.e., for example, 300 nm v. 50 nm); ii) microfluidization produces more stable particles than either milling or homogenization; and iii) microfluidization produces pH-resistant particles (i.e., stomach acid or small intestine base conditions) unlike those produced by either milling or homogenization.

Example 16: Improved Efficacy Over Conventional Nanoparticulate Compositions

This example will provide data showing that a uniform microfluidized nanoemulsion as contemplated by one embodiment of the present invention has improved efficacy in lowering plasma cholesterol levels that a conventional nanoparticulate composition.

The study will have duration of six (6) weeks. Briefly, seventy (70) hamsters will be fed a liquid-based hypercholesterolemic diet for a two (2) week pre-test period in order to elevate and stabilize plasma cholesterol levels. Subsequently, the hamsters are divided into the seven (7) test groups (n=10) shown below. Each group is maintained on the liquid-based hypercholesterolemic diet and: i) a nanoparticulate composition (i.e., for example, prepared as per the '202 Cooper et al. application); or ii) a uniform microfluidized nanoemulsion as contemplated by one embodiment of the present invention, for four (4) additional weeks.

Group I: Hypercholesterolemic diet only
Group II: Hypercholesterolemic diet+0.1% (w/w) plant sterol nanoparticulate composition.
Group III: Hypercholesterolemic diet+0.5% (w/w) plant sterol nanoparticulate composition.
Group IV: Hypercholesterolemic diet+1% (w/w) plant sterol nanoparticulate composition.
Group V: Hypercholesterolemic diet+0.1% (w/w) plant sterol uniform microfluidized nanoemulsion.
Group VI: Hypercholesterolemic diet+0.5% (w/w) plant sterol uniform microfluidized nanoemulsion.
Group VII: Hypercholesterolemic diet-f 1% (w/w) plant sterol uniform microfluidized nanoemulsion.

Blood samples are taken at 0, 2, 3, 4, 5, and 6 weeks where plasma cholesterol levels will be determined by methods known in the art.

A greater efficacy of the plant sterol uniform microfluidized nanoemulsions to lower plasma cholesterol levels is seen because: i) the average particle diameter of the uniform microfluidized nanoemulsion is smaller than the conventional nanoparticulate composition (i.e., for example, 300 nm v. 50 nm); ii) microfluidization produces more stable particles than either milling or homogenization; and iii) microfluidization produces pH-resistant particles (i.e., stomach acid or small intestine base conditions) unlike those produced by either milling or homogenization.

Example 17: Microfluidization Single Pass Comparison

This example provides data showing that the Bosch technique does not produce a uniform microfluidized nanoemulsion when compared to one embodiment of the present invention under identical microfluidization techniques.

Figure 20A:
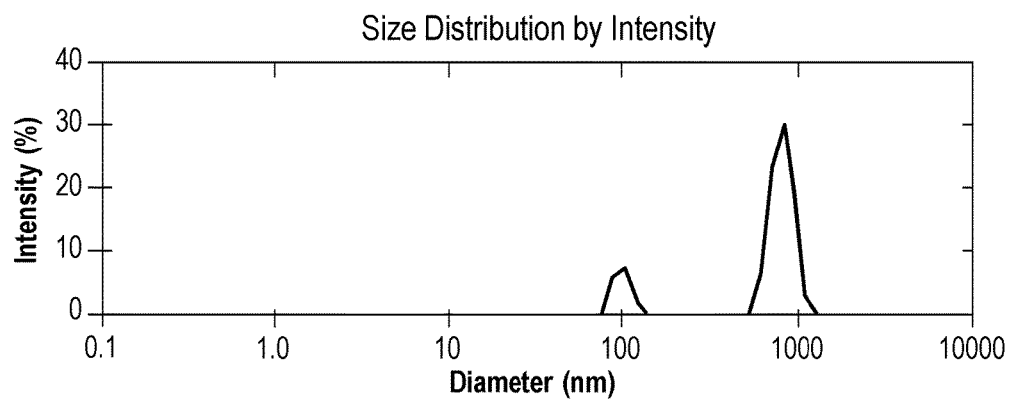
Figure 20B:
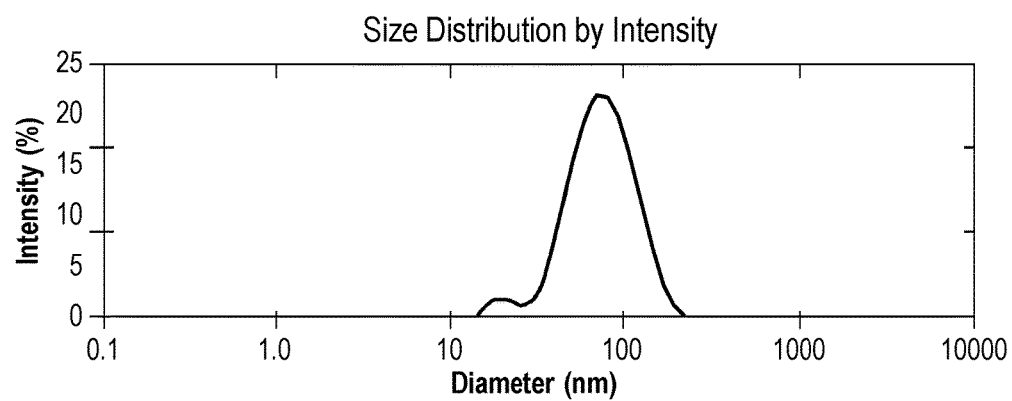

The Group I & II premixes were prepared in accordance with Example 13. Each premix was subjected to one pass at 25,000 PSI in the microfluidizer. Group I representing the Bosch formulation) shows that 85% of the particles have a mean diameter of 815 nm. See FIG. 20A. Group II (representing one embodiment of the present invention) shows that 98% of the particles have a mean diameter of 78 nm. See FIG. 20B This represents a greater than ten-fold difference in average diameter. Significantly, only 15% of the Bosch particles are within the 100 nm range, thereby representing a six-fold difference in particle diameter distribution in this lower range.

The average particle diameter distributions between Group I and Group II are presented in Tables 23 & 24 below.

TABLE 23

Microfluidized Cholesterol/Tween ® 80/Water Nanoemulsion: Single Pass

|  | Diam. (nm) | % Intensity | Width (nm) |
|---|---|---|---|
| Peak1 | 815.3 | 84.5 | 117.7 |
| Peak 2 | 101.8 | 15.54 | 10.54 |

Z-Average: 651.5;
PDI: 84.5;
Intercept: 0.7487

TABLE 24

Microfluidized Cholesterol/Oil/Lecithin/Tween ® 80/Water Nanoemulsion: Single Pass

|  | Diam. (nm) | % Intensity | Width (nm) |
|---|---|---|---|
| Peak1 | 78.43 | 97.47 | 31.43 |
| Peak 2 | 19.63 | 2.535 | 2.928 |

Z-Average: 65.98;
PDI: 0.190;
Intercept: 0.9210

The invention claimed is:
1. A method for making a nanoemulsion, comprising:
a) providing a premix comprising:
an oil-based medium, an aqueous medium,
an emulsifier, and optionally a compound to be delivered;
b) subjecting said premix to single-pass microfluidization with a microfluidizer;

wherein said method provides a uniform nanoemulsion comprising a population of nanoparticles, the nanoemulsion being uniform in that:

less than 3% of the nanoparticles in the population have a diameter outside the range of between approximately 10 and approximately 110 nanometers, and wherein the difference between the minimum diameter and maximum diameter of the nanoparticles in the population does not exceed 600 nm.

2. The method of claim 1, wherein said aqueous medium is selected from the group consisting of water, saline solution, ringers solution, and 5% dextrose.

3. The method of claim 1, wherein said oil-based medium is selected from the group consisting of saturated and unsaturated oils from vegetable and marine sources, silicone oils, and mineral oils.

4. The method of claim 1, wherein said compound is present and is selected from the group consisting of a plant sterol, cod liver oil, tocopherol, lecithin, lutein, zeaxanthin, and soy protein.

5. The method of claim 1, wherein said compound is present and is a pharmaceutical agent.

6. The method of claim 1, wherein said compound is present and is a nutraceutical agent.

7. The method of claim 1, wherein said compound is present and is a cosmeceutical agent.

8. The method of claim 1, wherein said compound is present and is a protein.

9. The method of claim 1, wherein the difference between the minimum and maximum diameters of the nanoparticles in the population does not exceed about 300 nm.

10. The method of claim 1, wherein the difference between the minimum and maximum diameters of the nanoparticles in the population does not exceed about 200 nm.

11. The method of claim 1, wherein the difference between the minimum and maximum diameters of the nanoparticles in the population does not exceed about 100 nm.

12. The method of claim 1, wherein the nanoparticle population has a minimum diameter of approximately 10 nanometers.

13. The method of claim 1, wherein the nanoparticle population has a minimum diameter of approximately 40 nanometers.

14. The method of claim 1, wherein the nanoparticle population has a minimum diameter of approximately 50 nanometers.

15. The method of claim 1, wherein the nanoemulsion is formulated for transdermal administration, oral administration, intravenous administration, intramuscular administration, or subcutaneous administration.

* * * * *